United States Patent
Aggarwal et al.

(10) Patent No.: US 9,943,547 B2
(45) Date of Patent: *Apr. 17, 2018

(54) MESENCHYMAL STEM CELLS AND USES THEREFOR

(71) Applicant: Mesoblast International Sárl, Meyrin (CH)

(72) Inventors: Sudeepta Aggarwal, North Potomac, MD (US); Mark F. Pittenger, Severna Park, MD (US); Timothy Varney, Baltimore, MD (US)

(73) Assignee: MESOBLAST INTERNATIONAL SÀRL, Meyrin (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/087,830

(22) Filed: Nov. 22, 2013

(65) Prior Publication Data

US 2014/0154276 A1    Jun. 5, 2014

Related U.S. Application Data

(63) Continuation of application No. 12/908,119, filed on Oct. 20, 2010, now abandoned, which is a continuation of application No. 11/541,853, filed on Oct. 2, 2006, now abandoned, which is a continuation-in-part of application No. 11/080,298, filed on Mar. 15, 2005, now abandoned.

(60) Provisional application No. 60/555,118, filed on Mar. 22, 2004.

(51) Int. Cl.
    *A61K 35/28*    (2015.01)
    *C12N 5/0775*   (2010.01)
    *A61K 38/20*    (2006.01)
    *A61K 45/06*    (2006.01)
    *A61K 35/12*    (2015.01)

(52) U.S. Cl.
    CPC .......... *A61K 35/28* (2013.01); *A61K 38/2026* (2013.01); *A61K 38/2066* (2013.01); *A61K 45/06* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *A61K 2035/124* (2013.01)

(58) Field of Classification Search
    CPC ............... A61K 35/28; A61K 38/2026; A61K 38/2066; C12N 5/0663; C12N 5/0675; C12N 5/066; C12N 5/06758; C12N 5/0665; C12N 5/0662; C12N 5/0664
    USPC ............... 435/325; 424/93.7, 184.1
    See application file for complete search history.

(56) References Cited

U.S. PATENT DOCUMENTS

| 5,486,359 | A | 1/1996 | Caplan et al. |
| 5,700,691 | A | 12/1997 | Bender et al. |
| 5,843,425 | A | 12/1998 | Sachs et al. |
| 6,010,696 | A | 1/2000 | Caplan et al. |
| 6,077,987 | A | 6/2000 | Breitbart et al. |
| 6,328,960 | B1 | 12/2001 | McIntosh et al. |
| 6,355,239 | B1 | 3/2002 | Bruder et al. |
| 6,497,875 | B1 | 12/2002 | Sorrell et al. |
| 9,694,035 | B2 | 7/2017 | Aggarwal et al. |
| 2002/0037278 | A1 | 3/2002 | Ueno et al. |
| 2002/0044923 | A1 | 4/2002 | Mosca et al. |
| 2002/0045260 | A1* | 4/2002 | Hung et al. ............ 435/368 |
| 2002/0064519 | A1 | 5/2002 | Bruder et al. |
| 2002/0110544 | A1 | 8/2002 | Goldberg et al. |
| 2003/0049843 | A1 | 3/2003 | Havenga et al. |
| 2003/0059412 | A1 | 3/2003 | Prockop et al. |
| 2003/0118567 | A1 | 6/2003 | Stewart |
| 2003/0139410 | A1 | 7/2003 | Sugaya et al. |
| 2004/0166097 | A1 | 8/2004 | Prockop et al. |
| 2005/0093044 | A1 | 5/2005 | Cheng et al. |
| 2005/0158397 | A1 | 7/2005 | Chopp et al. |
| 2005/0239897 | A1 | 10/2005 | Pittenger et al. |
| 2006/0112365 | A1 | 5/2006 | Ito et al. |
| 2014/0161776 | A1 | 6/2014 | Aggarwal et al. |
| 2014/0328807 | A1 | 11/2014 | Aggarwal et al. |
| 2015/0272997 | A1 | 10/2015 | Aggarwal et al. |

FOREIGN PATENT DOCUMENTS

| CN | 1382450 | 12/2002 |
| CN | 1536075 | 10/2004 |
| EP | 1279738 | 1/2003 |
| EP | 1391505 A1 | 2/2004 |
| JP | 1985-48933 | 4/1985 |
| JP | 1989-501792 | 6/1989 |
| JP | 2003-137898 | 5/2003 |
| JP | 2003-520254 | 7/2003 |
| JP | 2004-506598 | 3/2004 |
| JP | 2004-507454 | 3/2004 |
| JP | 2004-559434 | 3/2006 |

(Continued)

OTHER PUBLICATIONS

Garcia-Olmo et al., 2003, Int. J. Colorectal Dis. 18:451-454.*

(Continued)

*Primary Examiner* — Christopher M Babic
*Assistant Examiner* — Kelaginamane T Hiriyanna
(74) *Attorney, Agent, or Firm* — Sterne, Kessler, Goldstein & Fox P.L.L.C.

(57) ABSTRACT

Methods of treating autoimmune diseases, allergic responses, cancer, or inflammatory diseases in an animal, promoting would healing, repairing epithelial damage and promoting angiogenesis in an organ or tissue of an animal by administering to the animal mesenchymal stem cells in an effective amount.

21 Claims, 9 Drawing Sheets

(56) References Cited

FOREIGN PATENT DOCUMENTS

| | | |
|---|---|---|
| JP | 2006-510675 | 3/2006 |
| JP | 4554940 | 9/2010 |
| KR | 20040016785 | 2/2004 |
| KR | 20040022134 | 3/2004 |
| WO | 87/05518 | 9/1987 |
| WO | 96/30031 | 10/1996 |
| WO | 97/41208 | 11/1997 |
| WO | 98/20731 | 5/1998 |
| WO | 99/43286 A2 | 9/1999 |
| WO | 99/47163 | 9/1999 |
| WO | 99/51247 A1 | 10/1999 |
| WO | 99/51275 A2 | 10/1999 |
| WO | 00/06701 | 2/2000 |
| WO | 00/49136 | 8/2000 |
| WO | 0053795 | 9/2000 |
| WO | 01/32189 | 5/2001 |
| WO | 01/52904 | 7/2001 |
| WO | 01/62901 A2 | 8/2001 |
| WO | 01/80865 | 11/2001 |
| WO | 0208389 A2 | 1/2002 |
| WO | 02/64182 | 8/2002 |
| WO | 03/003090 A1 | 1/2003 |
| WO | 03/04661 | 1/2003 |
| WO | 03/10305 | 2/2003 |
| WO | 03/18077 | 3/2003 |
| WO | 03/020908 A2 | 3/2003 |
| WO | 03/039489 A2 | 5/2003 |
| WO | 03/59272 | 7/2003 |
| WO | 03/059276 | 7/2003 |
| WO | 03/68248 | 8/2003 |
| WO | 03/78567 | 9/2003 |
| WO | 03/78609 | 9/2003 |
| WO | 03/085099 A2 | 10/2003 |
| WO | 03/105908 | 12/2003 |
| WO | 04/003164 | 1/2004 |
| WO | 04/06942 | 1/2004 |
| WO | 04/07697 | 1/2004 |
| WO | 04/11621 | 2/2004 |
| WO | 2004/022579 | 3/2004 |
| WO | 2004/052177 | 6/2004 |
| WO | 04/084950 | 10/2004 |
| WO | 05/001076 | 1/2005 |
| WO | 05/013885 | 2/2005 |
| WO | 05/93044 | 10/2005 |
| WO | 06/112365 | 10/2006 |
| WO | 07/84354 | 7/2007 |
| WO | 2007/124594 | 11/2007 |

OTHER PUBLICATIONS

Oritz et al., 2003, Proc. Nat. Acad. Sci (USA) 14:8407-8411.*
Frassoni et al 2002, Bone Marrow Transplant 29: S2 , Abs. p. 1 of 1.*
Klyushenkova et al 1999, FASEB J. 13 (4): A615, Abs p. 1 of 1.*
Maitra et al Jan. 2004 Bone Marrow Transplantation 33:597-604.*
Okomoto et al 2002, Nature Medicine 8:1011-1017.*
Pittenger et al 1999, Science 284:143-147.*
Rasmusson et al 2003, Transplantation 76:1208-1213.*
Pittenger et al 1999, Sceince 284:143-147.*
Gao et al 2001 Cells Tissues Organs 169:12-20. Abs. pp. 1-2.*
van Laar J M & Tyndall, Rheumatology 45(1 0), 1187-1193, Oct. 2006 online Jun. 15, 2006.
"Stem Cells and Myocardial Regeneration," Marc S. Penn, Ed. Humana Press, Totowa NJ.
Aggarawal et al., "Human mesenchymal stem cells modulate allogeneic immune cell responses." Blood, vol. 105, No. 4, Feb. 15, 2005, pp. 1815-1822.
Al-Khaldi et al., Ann. Thoracic. Surg., 75:204-209 (2003).
Al-Khaldi et al., Gene Ther., 10:621-629 (2003).
Andreef, Blood, 102(11): 60a (2003).
Ballas et al., "Adult bone marrow stem cells for cell and gene therapies: implications for greater use." Journal Cellular Biochemistry, Supplement, vol. 38, p. 20, 2002.
Barry et al., Birth Defect Research (Part C) 69:250-256 (2003).
Bartholomew et al., "Mesenchymal stem cells suppress lymphocyte proliferation in vitro and prolong skin graft survival in vivo." Experimental Hematology, vol. 30, Issue 1, p. 42, Jan. 2002.
Brittan, J. Pathol., 197:492-509 (2002).
Carmeliet et al., "The emerging role of the bone marrow-derived stem cells in (therapeutic) angiogenesis" Thrombosis and Haemostasis, 86:289-297 (2001).
Chopp et al., "Spinal cord injury in rat: treatment with bone marrow stromal cell transplantation." Neuroreport, vol. 11, Issue 13, p. 3001, Sep. 11, 2000.
Chopp et al., The Lancet Neurology, 1:92-100 (2002).
Conese et al., J. Cystic Fibrosis, 5(3):141-143 (2006).
Database WPI Week 200679, Thomson Scientific, London, GB; XP002545400, AN 2006-781676, & WO 2006/112365 A (Japan Health Sci Found), Sep. 17, 2009.
DeKok et al., "Investigation of allogeneic mesenchymal stem cell-based alveolar bone formation: preliminary findings." Clinical Oral Implants Research, vol. 14, Issue 4, p. 48, Aug. 2003.
Devine et al., "Mesenchymal stem cells distribute to a wide range of tissues following systemic infusion into nonhuman primates." Blood 101(8):2999-3001; Apr. 15, 2003.
Devine et al., "Mesenchymal stem cells: stealth and suppression." Cancer Journal, Supplement 2, S76, Nov.-Dec. 2001.
DiNicola et al., "Human bone marrow stromal cells suppress T-lymphocyte proliferation induced by cellular or nonspecific mitogenic stimuli." Blood, vol. 99, Issue 10, p. 3838, May 15, 2002.
Dzionek et al., "BDCA-2, BDCA-3, and BDCA-4: three markers for distinct subsets of dendritic cells in human peripheral blood." Journal of Immunology, vol. 165, Issue 11, p. 6037, Dec. 1, 2000.
Eaves et al., "Characterization of human hematopoietic cells with short-lived in vivo repopulating activity." Annals of the New York Academy of Sciences, vol. 938, p. 63, Jun. 2001.
El-Badri et al., "Mesenchymal stem cells in autoimmune disease," Stem Cells and Development, 13:463-472 (2004) XP9145234.
European Communication pursuant to Article 94(3) EPC in EP 09009947.4-2107, dated May 21, 2010.
European Search Report in EP 07861373.4-1222, dated Mar. 2, 2009.
European Search Report in EP 09009947.4, dated Sep. 23, 2009.
Extended European Search Report in EP 09009947.4, dated Sep. 11, 2009.
Extended European Search Report in EP 10011225.9, dated Mar. 11, 2011.
Feng, "The differentiation of bone marrow-derived Mesenchymal stem cells in rat lung and their therapeutic effects to lung injury," Chinese Excellent Ph.D. Thesis Database, contribution for on-line publishing, Oct. 20, 2006.
Frassoni et al., Int. Society for Cell Therapy, SA006 (abstract) (2002).
Fukuda, "Development of regenerative cardiomyocytes from mesenchymal stem cells for cardiovascular tissue engineering." Artificial Organs, vol. 25, Issue 3, p. 187, Mar. 2001.
Garcia-Olmo et al., Int. J. Colorectal Dis., 18:451-454 (2003).
Goncalves, Bioessays, 27:506-517 (2005).
Guan Xiao Qing et al., "Study on Mesenchymal stem cells entering the brain through the blood-brain barrier," J. Pediatrics, 42(12):920-923 (2004) XP001525802 (Abstract).
Gupta et al., Therapeutic Applications. Leukemia, 15(12):1950-1961 (2001).
Hamada et al., "Mesenchymal stem cells (MSC) as therapeutic cytoreagents for gene therapy," Cancer Science, Japanese Cancer Associate, Tokyo, JP, 96(3):149-156 (2005) XP009145096.
Harris et al., "Prostaglandins as modulators of immunity." Trends in Immunology, vol. 23, No. 3, p. 144, Mar. 2002.
Haynesworth et al., "Characterization of cells with osteogenic potential from human marrow." Bone, vol. 13, p. 69, 1992.

(56) References Cited

OTHER PUBLICATIONS

Haynesworth et al., "Cytokine expression by human marrow-derived mesenchymal progenitor cells in vitro: effects of dexamethasone and IL-1 alpha." Journal of Cell Physiology, vol. 166, Issue 3, p. 585, Mar. 1996.
Hori et al., J. Surgical Research, 102:156-160 (2002).
Horwitz et al., "Clinical Responses to bone marrow transplantation in children with severe osteogenesis imperfecta." Blood, vol. 97, Issue 5, p. 1227, Mar. 2001.
Horwitz et al., "Isolated allogeneic bone marrow-derived mesenchymal cells engraft and stimulate growth in children with osteogenesis imperfecta: Implications for cell therapy of bone." vol. 99, Issue 13, 8932, Jun. 25, 2002.
Horwitz et al., Cytotherapy, 7(5):393-395 (2005).
Science Magazine, Multilineage Potential of Adult Human Mesenchymal Stem Cells, 1999—http://www.sciencemag.org/feature/data/983855.dtl.
Ikehara et al., Drugs Today, 38:103-111 (2002).
International Preliminary Report on Patentability in PCT/US07/20724, dated Apr. 16, 2009.
International Preliminary Report on Patentability in PCT/US08/57828, dated Oct. 1, 2009.
International Search Report and Written Opinion in PCT/US07/20724, dated Apr. 17, 2008.
International Search Report and Written Opinion in PCT/US08/57828, dated Jan. 29, 2009.
International Search Report in PCT/US03/01129, dated Sep. 16, 2003.
International Search Report in PCT/US05/08506, dated Jul. 7, 2005.
International Search Report in PCT/US07/20724, dated Apr. 17, 2008.
Oswald et al Jan. 2004, Stem Cells 22:377-384.
Japanese Patent Office, Notice of Reasons for Rejection in Application No. 2014-124452, dated Jun. 19, 2015 (9 pages).
Semont et al. Mar. 2006, Adv. Exp. Med. Biol. 585-19-30 Abstract p. 2 of 2.
Maitra et al. Jan. 2004, Bone Marrow Transplantation 33:597-604.
Notice of Preliminary Rejection for Korean Application No. 10-2015-7002664, dated Feb. 23, 2016.
Bell, "IgE, allergies and helminth parasites: A new perspective on an old conundrum," Immunology and Cell Biology, 74, pp. 337-345, 1996.
Office Action in U.S. Appl. No. 14/138,577, dated Feb. 2, 2016.
Osamu Date, et al., "Study on revascularization by bone marrow Mesenchymal stem cells," Angiology, Japan, issued Sep. 25, 2003, vol. 43, No. 9, p. 557.
Osamu Date, et al., "Investigation of the expansion of bone marrow mesenchymal stem cells in a mouse model of hind limb ischemia and angiogenesis by the transplantation of the cells," Japanese Journal of Cardiovascular Surgery, Japan, issued on Jan. 26, 2004, vol. 33, Supplement, 285.
Office Action for Japanese Patent App. No. 2012-58539, dated Feb. 18, 2016.
Notice of Opposition against European Application No. 10011225.9, 26 pages, 2016.
Boucher, "New concepts of the pathogensis of cystic fibrosis lung disease," Eur. Respir J., 23, pp. 146-158, 2004.
Durie et al., Characteristic Multiorgan Pathology of Cystic Fibrosis in a Long-Living Cystic Fibrosis Transmembrane Regulator Knockout Murine Model, American Journal of Pathology, vol. 164, No. 4, pp. 1481-1493 2004.
Grom, Natural Killer Cell Dysfunction, Arthritis & Rheumatism, vol. 50, No. 3, pp. 689-698, 2004.
Kotton et al., "Bone marrow-derived cells as progenitors of lung alveolar epithelium," Development, 128, pp. 5181-5188,2001.
Kraue et al., "Multi-Organ, Multi-Lineage Engraftment by a Single Bone Marrow-Derived Stem Cell," Cell, vol. 105, pp. 369-377, 2001.
McCombs, "Research in Cystic Fibrosis: A Review," Texas Reports on Biology and Medicine, pp. 616-629, 1973.
Pichler et al., Praklinische Untersuchung von alpha1-saurem Glykoprotein (Orosomucoid), Wien Klin Wuchenschr, pp. 192-198, 1999.
Selman et al, "Idiopathic Pulmonary Fibrosis, Pathgenesis and Therapeutic Approaches," Drugs, 64, pp. 405-430.
Saunders Company, "Pathologic Basis of Disease," 9 pages, 1982.
King et al., "Idiopathic Pulmonary Fibrosis, Relationship between Histopathologic Features and Mortality," Am J. Respir Crit Care Med., pp. 1025-1032, 2001.
King, "Idiopathic Interstitial Pneumonias: Progress in Classification, Diagnosis, Pathogenesis and Management," Transactions of the American Clinical and Climatological Association, vol. 115, pp. 43-78, 2004.
Thannickal et al., "Mechanisms of Pulmonary Fibrosis," Anu. Rev. Med., pp. 395-417, 2004.
Ziobro et al., Ceramide Mediates lung fibrosis in cystic fibrosis,' Annu. Rev. Med., pp. 705-709, 2013.
Office Action in Application No. 10 011 224.2 dated Aug. 22, 2016.
Miguel et al, "Immunosuppressive Properties of Mesenchymal Stem Cells: Advances and Applications," Current Molecular Medicine, pp. 574-591, 2012.
Komori et al., "Involvement of bone marrow-derived cells in healing of experimental colitis in rats", Wound Repair and Regeneration, vol. 13, No. 1, pp. 109-118, 2005.
Extended European Search Report for European Application No. 16 171 424.1, dated Oct. 25, 2016.
Japanese Office Action for Patent Application No. 2012-058539, dated Sep. 13, 2016.
Bouma et al., "The immunological and genetic basis of inflammatory bowel disease," Nature Reviews Immunology 3, 521-533, 2003. (Abstract only—will need to get article at some point.).
Merck Manual, 17th ed., Japanese version, published Dec. 10, 1999, pp. 305 and 308.
Office Action in U.S. Appl. No. 14/334,128, dated Oct. 22, 2014.
Deng et al., (2003, Chin. Med. J. 116: 1649-1654 pp. 1-4).
Izadpanah, et al. J. Cell Biochem. Biologic Properties of Mesenchymal Stem Cells Derived from Bone Marrow and Adipose tissue, Dec. 1, 2006, 99(5): 1285-1297.
Melgar, et al. Over-expression of Interleukin 10 in Mucosal T cells of Patients with Active Ulcerative Colitis, Clin. Exp Immunol 2003; 134:127-137.
Barry F, et al., The SH-3 and SH-4 Antibodies Recognize Distinct Epitopes on CD73 from Human Mesenchymal Stem Cells, Biochem. Bioph. Res. Co., 2001, vol. 289, pp. 519-524.
Dominici M, et al., Minimal criteria for defining multipotent mesenchymal stromal cells. The International Society for Cellular Therapy position statement, Cytotherapy, 2006, vol. 8, No. 4, pp. 315-317.
Ikehara S., Treatment of autoimmune diseases by a new bone marrow transplantation method, Journal of Clinical and Experimental Medicine (Igakunoayumi), 2005, vol. 213, No. 1, pp. 96-98.
Saijo Y., Oncogene therapy using mesenchymal stem cells, Respiratory Molecular Medicine, 2004, vol. 8, No. 5, pp. 34-38.
Kushida et al., 2001, Stem Cells, 19:226-235.
Jones et al., 2005, MedGenMed, 7:16.
Le Blanc et al., 2004, The Lancet, 363:1439-1441.
Muraro et al., 2004, Cytotherapy, 6:615-620.
Meisel et al., 2004, Blood, 1003:4619-4621.
Ishida et al., 1994, J. of Immunology, 152:3119-3127.
Oritz et al., 2003, PNAS, 100:8407-8411.
Burt et al., 2003, Bone Marrow Transplantation, 31:521-524.
Bruck et al., 2003, J. Neurological Sciences, 206:181-185.
Akiyama et al., 2002, J. of Neuroscience, 22:6623-6630.
Koc, ON, et al. "Allogeneic mesenchymal stem cell infusion for treatment of metachromatic leukodystrophy (MLD) and Hurler Syndrome (MPS-IH)," Bone Marrow Transplantation 30:215-222 (2002), 8 pages.
Ditschkowski, M., et al. "Improvement of inflammatory bowel disease after allogeneic stem-cell transplantation," Transplantation 75:1745-1747 (2003), 3pages.
Office Action dated Nov. 13, 2017, in U.S. Appl. No. 14/138,577, Aggarwal, S. et al., filed Dec. 23, 2013, 10 pages.

(56) References Cited

OTHER PUBLICATIONS

Office Action dated Apr. 17, 2017, in U.S. Appl. No. 14/138,577, Aggarwal, S. et al., filed Dec. 23, 2013, 14 pages.
Office Action dated Apr. 2, 2015, in U.S. Appl. No. 14/138,577, Aggarwal, S. et al., filed Dec. 23, 2013, 10 pages.
Office Action dated Nov. 17, 2016, in U.S. Appl. No. 14/305,240, Aggarwal, S. et al., filed Jun. 16, 2014, 15 pages.
Office Action dated Feb. 8, 2016, in U.S. Appl. No. 14/305,240, Aggarwal, S. et al., filed Jun. 16, 2014, 14 pages.
Office Action dated Oct. 5, 2015, in U.S. Appl. No. 14/305,240, Aggarwal, S. et al., filed Jun. 16, 2014, 10 pages.
Office Action dated Jan. 2, 2015, in U.S. Appl. No. 14/305,240, Aggarwal, S. et al., filed Jun. 16, 2014, 12 pages.
Office Action dated Sep. 28, 2015, in U.S. Appl. No. 14/334,128, Aggarwal, S. et al., filed Jul. 17, 2014, 10 pages.
Office Action dated Jan. 27, 2017, in U.S. Appl. No. 14/739,924, Aggarwal, S. et al., filed Jun. 15, 2015, 9 pages.
Office Action dated Jul. 12, 2016, in U.S. Appl. No. 14/739,924, Aggarwal, S. et al., filed Jun. 15, 2015, 7 pages.
Office Action dated Nov. 25, 2015, in U.S. Appl. No. 14/739,924, Aggarwal, S. et al., filed Jun. 15, 2015, 9 pages.

\* cited by examiner

MESENCHYMAL STEM CELLS AND USES THEREFOR

RELATED APPLICATIONS

This application is a continuation of Ser. No. 12/908,119, filed Oct. 20, 2010, which is a continuation of U.S. patent application Ser. No. 11/541,853, filed Oct. 2, 2006, now abandoned, which is a continuation-in-part of U.S. patent application Ser. No. 11/080,298, filed Mar. 15, 2005, now abandoned, which claims priority based on U.S. Provisional Patent Application Ser. No. 60/555,118, filed Mar. 22, 2004, the contents of which are incorporated by reference in their entireties.

FEDERALLY SPONSORED RESEARCH OR DEVELOPMENT

The invention was made with Government support under Contract No. N66001-02-C-8068 awarded by the Department of the Navy. The Government has certain rights in this invention.

BACKGROUND OF THE INVENTION

This invention relates to mesenchymal stem cells. More particularly, this invention relates to novel uses for mesenchymal stem cells, including promoting angiogenesis in various tissues and organs, treating autoimmune diseases, treating allergic responses, treating cancer, treating inflammatory diseases and disorders, promoting would healing, treating inflammation, and repairing epithelial damage.

Mesenchymal stem cells (MSCs) are multipotent stem cells that can differentiate readily into lineages including osteoblasts, myocytes, chondrocytes, and adipocytes (Pittenger, et al., *Science*, Vol. 284, pg. 143 (1999); Haynesworth, et al., *Bone*, Vol. 13, pg. 69 (1992); Prockop, *Science*, Vol. 276, pg. 71 (1997)). In vitro studies have demonstrated the capability of MSCs to differentiate into muscle (Wakitani, et al., *Muscle Nerve*, Vol. 18, pg. 1417 (1995)), neuronal-like precursors (Woodbury, et al., *J. Neurosci. Res.*, Vol. 69, pg. 908 (2002); Sanchez-Ramos, et al., *Exp. Neurol.*, Vol. 171, pg. 109 (2001)), cardiomyocytes (Toma, et al., *Circulation*, Vol. 105, pg. 93 (2002); Fakuda, *Artif. Organs*, Vol. 25, pg. 187 (2001)) and possibly other cell types. In addition, MSCs have been shown to provide effective feeder layers for expansion of hematopoietic and embryonic stem cells (Eaves, et al., *Ann. N.Y. Acad. Sci.*, Vol. 938, pg. 63 (2001); Wagers, et al., *Gene Therapy*, Vol. 9, pg. 606 (2002)). Recent studies with a variety of animal models have shown that MSCs may be useful in the repair or regeneration of damaged bone, cartilage, meniscus or myocardial tissues (DeKok, et al., *Clin. Oral Implants Res.*, Vol. 14, pg. 481 (2003)); Wu, et al., *Transplantation*, Vol. 75, pg. 679 (2003); Noel, et al., *Curr. Opin. Investig. Drugs*, Vol. 3, pg. 1000 (2002); Ballas, et al., *J. Cell. Biochem. Suppl.*, Vol. 38, pg. 20 (2002); Mackenzie, et al., *Blood Cells Mol. Dis.*, Vol. 27 (2002)). Several investigators have used MSCs with encouraging results for transplantation in animal disease models including osteogenesis imperfecta (Pereira, et al., *Proc. Nat. Acad. Sci.*, Vol. 95, pg. 1142 (1998)), parkinsonism (Schwartz, et al., *Hum. Gene Ther.*, Vol. 10, pg. 2539 (1999)), spinal cord injury (Chopp, et al., *Neuroreport*, Vol. 11, pg. 3001 (2000); Wu, et al., *J. Neurosci. Res.*, Vol. 72, pg. 393 (2003)) and cardiac disorders (Tomita, et al., *Circulation*, Vol. 100, pg. 247 (1999). Shake, et al., *Ann. Thorac. Surg.*, Vol. 73, pg. 1919 (2002)). Importantly, promising results also have been reported in clinical trials for osteogenesis imperfecta (Horwitz, et al., *Blood*, Vol. 97, pg. 1227 (2001); Horowitz, et al. *Proc. Nat. Acad. Sci.*, Vol. 99, pg. 8932 (2002)) and enhanced engraftment of heterologous bone marrow transplants (Frassoni, et al., *Int. Society for Cell Therapy*, SA006 (abstract) (2002); Koc, et al., *J. Clin. Oncol.*, Vol. 18, pg. 307 (2000)).

MSCs express major histocompatibility complex (MHC) class I antigen on their surface but do not express MHC class II (Le Blanc, et al., *Exp. Hematol.*, Vol. 31, pg. 890 (2003); Potian, et al., *J. Immunol.*, Vol. 171, pg. 3426 (2003)) and no B7 or CD40 co-stimulatory molecules (Majumdar, et al., *J. Biomed. Sci.*, Vol. 10, pg. 228 (2003)), suggesting that these cells have a low-immunogenic phenotype (Tse, et al., *Transplantation*, Vol. 75, pg. 389 (2003)). MSCs also inhibit T-cell proliferative responses in an MHC-independent manner (Bartholomew, et al., *Exp. Hematol.*, Vol. 30, pg. 42 (2002); Devine, et al., *Cancer J.*, Vol. 7, pg. 576 (2001); DiNicola, et al., *Blood*, Vol. 99, pg. 3838 (2002)). These immunological properties of MSCs may enhance their transplant engraftment and limit the ability of the recipient immune system to recognize and reject allogeneic cells following transplantation. The production of factors by MSCs, that modulate the immune response and support hematopoiesis together with their ability to differentiate into appropriate cell types under local stimuli make them desirable stem cells for cellular transplantation studies (Majumdar, et al., *Hematother. Stem Cell Res.*, Vol. 9, pg. 841 (2000); Haynesworth, et al., *J. Cell. Physiol.*, Vol. 166, pg. 585 (1996).

BRIEF SUMMARY OF THE INVENTION

Applicants presently have examined the interactions of mesenchymal stem cells with isolated immune cell populations, including dendritic cells (DC1 and DC2), effector T-cells (Th1 and Th2), and NK cells. Based on such interactions, Applicants discovered that mesenchymal stem cells may regulate the production of various factors that may regulate several steps in the immune response process. Thus, the mesenchymal stem cells may be employed in the treatment of disease conditions and disorders involving the immune system, or diseases, conditions, or disorders involving inflammation, epithelial damage, or allergic responses. Such diseases, conditions, and disorders include, but are not limited to, autoimmune diseases, allergies, arthritis, inflamed wounds, alopecia araeta (baldness), periodontal diseases including gingivitis and periodontitis, and other diseases, conditions or disorders involving an immune response.

In addition, it is believed that mesenchymal stem cells express and secrete vascular endothelial growth factor, or VEGF, which promotes angiogenesis by stimulating the formation of new blood vessels. Mesenchymal stem cells also stimulate peripheral blood mononuclear cells (PBMCs) to produce VEGF.

Furthermore, it is believed that mesenchymal stem cells stimulate dendritic cells (DCs) to produce Interferon-Beta (IFN-β), which promotes tumor suppression and immunity against viral infection.

DETAILED DESCRIPTION OF THE INVENTION

In accordance with an aspect of the present invention, there is provided a method of treating a disease selected from the group consisting of autoimmune diseases and graft-versus-host disease in an animal. The method comprises administering to the animal mesenchymal stem cells in an amount effective to treat the disease in the animal.

Although the scope of this aspect of the present Invention is not to be limited to any theoretical reasoning, it is believed that at least one mechanism by which the mesenchymal stem cells suppress autoimmune disease and graft-versus-host disease is by causing the release of Interleukin-10 (IL-10) from regulatory T-cells ($T_{reg}$ cells) and/or dendritic cells (DC).

Autoimmune diseases which may be treated in accordance with the present invention include, but are not limited to, multiple sclerosis, Type 1 diabetes, rheumatoid arthritis, uveitis, autoimmune thyroid disease, inflammatory bowel disease, scleroderma, Graves' Disease, lupus, Crohn's disease, autoimmune lymphoproliferative disease (ALPS), demyelinating disease, autoimmune encephalomyelitis, autoimmune gastritis (AIG), and autoimmune glomerular diseases. Also, as noted hereinabove, graft-versus-host disease may be treated. It is to be understood, however, that the scope of the present invention is not to be limited to the treatment of the specific diseases mentioned herein.

In one embodiment, the animal to which the mesenchymal stem cells are administered is a mammal. The mammal may be a primate, including human and non-human primates.

In general, the mesenchymal stem cell (MSC) therapy is based, for example, on the following sequence: harvest of MSC-containing tissue, isolation and expansion of MSCs, and administration of the MSCs to the animal, with or without biochemical or genetic manipulation.

The mesenchymal stem cells that are administered may be a homogeneous composition or may be a mixed cell population enriched in MSCs. Homogeneous mesenchymal stem cell compositions may be obtained by culturing adherent marrow or periosteal cells, and the mesenchymal stem cell compositions may be obtained by culturing adherent marrow or periosteal cells, and the mesenchymal stem cells may be identified by specific cell surface markers which are identified with unique monoclonal antibodies. A method for obtaining a cell population enriched in mesenchymal stem cells is described, for example, in U.S. Pat. No. 5,486,359. Alternative sources for mesenchymal stem cells include, but are not limited to, blood, skin, cord blood, muscle, fat, bone, and perichondrium.

Compositions having greater than about 95%, usually greater than about 98%, of human mesenchymal stem cells can be achieved using techniques for isolation, purification, and culture expansion of mesenchymal stem cells. For example, isolated, cultured mesenchymal stem cells may comprise a single phenotypic population (about 95% or about 98% homogeneous) by flow cytometric analysis of expressed surface antigens. The desired cells in such composition are identified as expressing a cell surface marker (e.g., CD73 or CD105) specifically bound by an antibody produced from hybridoma cell line SH2, ATCC accession number HB 10743; an antibody produced from hybridoma cell line SH3, ATCC accession number HB 10744; or an antibody produced from hybridoma cell line SH4, ATCC accession number HB 10745.

The mesenchymal stem cells may be administered by a variety of procedures. The mesenchymal stem cells may be administered systemically, such as by intravenous, intraarterial, or intraperitoneal administration.

The mesenchymal stem cells may be from a spectrum of sources including autologous, allogeneic, or xenogeneic.

The mesenchymal stem cells are administered in an amount effective to treat an autoimmune disease or graft-versus-host disease in an animal. The mesenchymal stem cells may be administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The amount of mesenchymal stem cells to be administered is dependent upon a variety of factors, including the age, weight, and sex of the patient, the autoimmune disease to be treated, and the extent and severity thereof.

The mesenchymal stem cells may be administered in conjunction with an acceptable pharmaceutical carrier. For example, the mesenchymal stem cells may be administered as a cell suspension in a pharmaceutically acceptable liquid medium or gel for injection or topical application.

In accordance with another aspect of the present invention, there is provided a method of treating an inflammatory response in an animal. The method comprises administering to the animal mesenchymal stem cells in an amount effective to treat the inflammatory response in the animal.

Although the scope of this aspect of the present invention is not to be limited to any theoretical reasoning, it is believed that the mesenchymal stem cells promote T-cell maturation to regulatory T-cells ($T_{reg}$), thereby controlling inflammatory responses. It is also believed that the mesenchymal stem cells inhibit T helper 1 cells (Th1 cells), thereby decreasing the expression of the Interferon-γ), (IFN-γ) in certain inflammatory reactions, such as those associated with psoriasis, for example.

In one embodiment, the inflammatory responses which may be treated are those associated with psoriasis.

In another embodiment, the mesenchymal stem cells may be administered to an animal such that the mesenchymal stem cells contact microglia and/or astrocytes in the brain to reduce inflammation, whereby the mesenchymal stem cells limit neurodegeneration caused by activated glial cells in diseases, or disorders such as Alzheimer's Disease, Parkinson's Disease, stroke, or brain cell injuries.

In yet another embodiment, the mesenchymal stem cells may be administered to an animal such that the mesenchymal stem cells contact keratinocytes and Langerhans cells in the epidermis of the skin to reduce inflammation as may occur in psoriasis, chronic dermatitis, and contact dermatitis. Although this embodiment is not to be limited to any theoretical reasoning, it is believed that the mesenchymal stem cells may contact the keratinocytes and Langerhans cells in the epidermis, and alter the expression of T-cell receptors and cytokine secretion profiles, leading to decreased expression of tumor necrosis factor-alpha (TNF-α) and increased regulatory T-cell ($T_{reg}$ cell) population.

In a further embodiment, the mesenchymal stem cells may be used to reduce inflammation in the bone, as occurs in arthritis and arthritis-like conditions, including but not limited to, osteoarthritis and rheumatoid arthritis, and other arthritic diseases listed in the website www.arthritis.org/conditions/diseases. Although the scope of this embodiment is not intended to be limited to any theoretical reasoning, it is believed that the mesenchymal stem cells may inhibit Interleukin-17 secretion by memory T-cells in the synovial fluid.

In another embodiment, the mesenchymal stem cells may be used to limit inflammation in the gut and liver during Inflammatory bowel disease and chronic hepatitis, respectively. Although the scope of this aspect of the present invention is not intended to be limited to any theoretical reasoning, it is believed that the mesenchymal stem cells promote increased secretion of Interleukin-10 (IL-10) and the generation of regulatory T-cells ($T_{reg}$ cells).

In another embodiment, the mesenchymal stem cells may be used to inhibit excessive neutrophil and macrophage activation in pathological conditions such as sepsis and trauma, including burn injury, surgery, and transplants. Although the scope of this embodiment is not to be limited to any theoretical reasoning, it is believed the mesenchymal stem cells promote secretion of suppressive cytokines such as IL-10, and inhibit macrophage migration inhibitory factor.

In another embodiment, the mesenchymal stem cells may be used to control inflammation in immune privileged sites such as the eye, including the cornea, lens, pigment epithelium, and retina, brain, spinal cord, pregnant uterus and placenta, ovary, testes, adrenal cortex, liver, and hair follicles. Although the scope of this embodiment is not to be limited to any theoretical reasoning, it is believed that the mesenchymal stem cells promote the secretion of suppressive cytokines such as IL-10 and the generation of $T_{reg}$ cells.

In yet another embodiment, the mesenchymal stem cells may be used to treat tissue damage associated with end-stage renal disease (ESRD) infections during dialysis and/or glomerulonephritis. Although the scope of this embodiment is not to be limited to any theoretical reasoning, it is believed that mesenchymal stem cells may promote renal repair. Mesenchymal stem cells also express and secrete vascular endothelial growth factor, or VEGF, which stimulates new blood vessel formation, which should aid in the repair of damaged kidney tissue.

In a further embodiment, the mesenchymal stem cells may be used to control viral infections such as influenza, hepatitis C, Herpes Simplex Virus, vaccinia virus infections, and Epstein-Barr virus. Although the scope of this embodiment is not to be limited to any theoretical reasoning, it is believed that the mesenchymal stem cells promote the secretion of Interferon-Beta (IFN-β).

In yet another embodiment, the mesenchymal stem cells may be used to control parasitic infections such as Leishmania infections and Helicobacter infections. Although the scope of this embodiment is not to be limited to any theoretical reasoning, it is believed that the mesenchymal stem cells mediate responses by T helper 2 (Th2) cells, and thereby promote increased production of Immunoglobulin E (IgE) by β-cells.

It is to be understood, however, that the scope of this aspect of the present invention is not to be limited to the treatment of any particular inflammatory response.

The mesenchymal stem cells may be administered to a mammal, including human and non-human primates, as hereinabove described.

The mesenchymal stem cells also may be administered systemically, as hereinabove described. Alternatively, in the case of osteoarthritis or rheumatoid arthritis, the mesenchymal stem cells may be administered directly to an arthritic joint.

The mesenchymal stem cells are administered in an amount effective to treat an inflammatory response in an animal. The mesenchymal stem cells may be administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact dosage of mesenchymal stem cells to be administered is dependent upon a variety of factors, including the age, weight, and sex of the patient, the inflammatory response being treated, and the extent and severity thereof.

The mesenchymal stem cells may be administered in conjunction with an acceptable pharmaceutical carrier, as hereinabove described.

In accordance with another aspect of the present invention, there is provided a method of treating inflammation and/or repairing epithelial damage in an animal. The method comprises administering to the animal mesenchymal stem cells in an amount effective to treat the inflammation and/or epithelial damage in the animal.

Although the scope of this aspect of the present invention is not to be limited to any theoretical reasoning, it is believed that the mesenchymal stem cells cause a decrease in the secretion of the pro-inflammatory cytokines TNF-α and Interferon-γ by T-cells, and an increase in the secretion of the anti-inflammatory cytokines Interleukin-10 (IL-10) and Interleukin-4 (IL-4) by T-cells. It is also believed that the mesenchymal stem cells cause a decrease in Interferon-γ secretion by natural killer (NK) cells.

The inflammation and/or epithelial damage which may be treated in accordance with this aspect of the present invention includes, but is not limited to, inflammation and/or epithelial damage caused by a variety of diseases and disorders, including, but not limited to, autoimmune disease, rejection of transplanted organs, burns, cuts, lacerations, and ulcerations, including skin ulcerations and diabetic ulcerations.

In one embodiment, the mesenchymal stem cells are administered to an animal in order to repair epithelial damage resulting from autoimmune diseases, including, but not limited to, rheumatoid arthritis, Crohn's Disease, Type 1 diabetes, multiple sclerosis, scleroderma, Graves' Disease, lupus, inflammatory bowel disease, autoimmune gastritis (AIG), and autoimmune glomerular disease. The mesenchymal stem cells also may repair epithelial damage resulting from graft-versus-host disease (GVHD).

This aspect of the present invention is applicable particularly to the repair of epithelial damage resulting from graft-versus-host disease, and more particularly, to the repair of epithelial damage resulting from severe graft-versus-host disease, including Grades III and IV graft-versus-host disease affecting the skin and/or the gastrointestinal system. Applicants have discovered, in particular, that mesenchymal stem cells, when administered to a patient suffering from severe graft-versus-host disease, and in particular, Grades III and IV gastrointestinal graft-versus-host disease, the administration of the mesenchymal stem cells resulted in repair of skin and/or ulcerated intestinal epithelial tissue in the patient.

In another embodiment, the mesenchymal stem cells are administered to an animal in order to repair epithelial damage to a transplanted organ or tissue including, but not limited to, kidney, heart, and lung, caused by rejection of the transplanted organ or tissue.

In yet another embodiment, the mesenchymal stem cells are administered to an animal to repair epithelial damage caused by burns, cuts, lacerations, and ulcerations, including, but not limited to, skin ulcerations and diabetic ulcerations.

The mesenchymal stem cells may be administered to a mammal, including human and non-human primates, as hereinabove described.

The mesenchymal stem cells also may be administered systemically, as hereinabove described.

The mesenchymal stem cells are administered in an amount effective to repair epithelial damage in an animal. The mesenchymal stem cells may be administered in an amount of from about $1\times10^5$ cells/kg to about $1\times10^7$ cells/ kg. In another embodiment, the mesenchymal stem cells are administered in an amount of from about $1\times10^6$ cells/kg to about $5\times10^6$ cells/kg. The exact dosage of mesenchymal stem cells to be administered is dependent upon a variety of factors, including the age, weight, and sex of the patient, the type of epithelial damage being repaired, and the extent and severity thereof.

In accordance with yet another aspect of the present invention, there is provided a method of treating cancer in an animal. The method comprises administering to the animal mesenchymal stem cells in an amount effective to treat cancer in the animal.

Although the scope of this aspect of the present invention is not to be limited to any theoretical reasoning, it is believed that the mesenchymal stem cells interact with dendritic cells, which leads to IFN-β secretion, which in turn acts as a tumor suppressor. Cancers which may be treated include, but are not limited to, hepatocellular carcinoma, cervical cancer, pancreatic cancer, prostate cancer, fibrosarcoma, medullablastoma, and astrocytoma. It is to be understood, however, that the scope of the present invention is not to be limited to any specific type of cancer.

The animal may be a mammal, including human and non-human primates, as hereinabove described.

The mesenchymal stem cells are administered to the animal in an amount effective to treat cancer in the animal. In general, the mesenchymal stem cells are administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact amount of mesenchymal stem cells to be administered is dependent upon a variety of factors, including the age, weight, and sex of the patient, the type of cancer being treated, and the extent and severity thereof.

The mesenchymal stem cells are administered in conjunction with an acceptable pharmaceutical carrier, and may be administered systemically, as hereinabove described. Alternatively, the mesenchymal stem cells may be administered directly to the cancer being treated.

In accordance with still another aspect of the present invention, there is provided a method of treating an allergic disease or disorder in an animal. The method comprises administering to the animal mesenchymal stem cells in an amount effective to treat the allergic disease or disorder in the animal.

Although the scope of this aspect of the present invention is not to be limited to any theoretical reasoning, it is believed that mesenchymal stem cells, when administered after an acute allergic response, provide for inhibition of mast cell activation and degranulation. Also, it is believed that the mesenchymal stem cells downregulate basophil activation and inhibit cytokines such as TNF-α, chemokines such as Interleukin-8 and monocyte chemoattractant protein, or MCP-1, lipid mediators such as leukotrienes, and inhibit main mediators such as histamine, heparin, chondroitin sulfates, and cathepsin.

Allergic diseases or disorders which may be treated include, but are not limited to, asthma, allergic rhinitis, atopic dermatitis, and contact dermatitis. It is to be understood, however, that the scope of the present invention is not to be limited to any specific allergic disease or disorder.

The mesenchymal stem cells are administered to the animal in an amount effective to treat the allergic disease or disorder in the animal. The animal may be a mammal. The mammal may be a primate, including human and non-human primates. In general, the mesenchymal stem cells are administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact dosage is dependent upon a variety of factors, including the age, weight, and sex of the patient, the allergic disease or disorder being treated, and the extent and severity thereof.

The mesenchymal stem cells may be administered in conjunction with an acceptable pharmaceutical carrier, as hereinabove described. The mesenchymal stem cells may be administered systemically, such as by intravenous or intraarterial administration, for example.

In accordance with a further aspect of the present invention, there is provided a method of promoting wound healing in an animal. The method comprises administering to the animal mesenchymal stem cells in an amount effective to promote wound healing in the animal.

Although the scope of the present invention is not to be limited to any theoretical reasoning, it is believed that, as mentioned hereinabove, the mesenchymal stem cells cause $T_{reg}$ cells and dendritic cells to release Interleukin-10 (IL-10). The IL-10 limits or controls inflammation in a wound, thereby promoting healing of a wound.

Furthermore, the mesenchymal stem cells may promote wound healing and fracture healing by inducing secretion factors by other cell types. For example, the mesenchymal stem cells may induce prostaglandin E2 ($PGE_2$)-mediated release of vascular endothelial growth factor (VEGF) by peripheral blood mononuclear cells (PBMCs), as well as $PGE_2$-mediated release of growth hormone, insulin, insulin-like growth factor 1 (IGF-1) insulin-like growth factor binding protein-3 (IGFBP-3), and endothelin-1.

Wounds which may be healed include, but are not limited to, those resulting from cuts, lacerations, burns, and skin ulcerations.

The mesenchymal stem cells are administered to the animal in an amount effective to promote wound healing in the animal. The animal may be a mammal, and the mammal may be a primate, including human and non-human primates. In general, the mesenchymal stem cells are administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact amount of mesenchymal stem cells to be administered is dependent upon a variety of factors, including the age, weight, and sex of the patient, and the extent and severity of the wound being treated.

The mesenchymal stem cells may be administered in conjunction with an acceptable pharmaceutical carrier, as hereinabove described. The mesenchymal stem cells may be administered systemically, as hereinabove described. Alternatively, the mesenchymal stem cells may be administered directly to a wound, such as in a fluid on a dressing or reservoir containing the mesenchymal stem cells.

In accordance with yet another aspect of the present invention, there is provided a method of treating or preventing fibrosis in an animal. The method comprises administering to the animal mesenchymal stem cells in an amount effective to treat or prevent fibrosis in an animal.

The mesenchymal stem cells may be administered to the animal in order to treat or prevent any type of fibrosis in the animal, including, but not limited to, cirrhosis of the liver, fibrosis of the kidneys associated with end-stage renal disease, and fibrosis of the lungs, including, but not limited to, Acute Respiratory Diseases Syndrome (ARDS) and chronic obstructive pulmonary disease (COPD). It is to be understood that the scope of the present invention is not to be limited to any specific type of fibrosis.

The mesenchymal stem cells are administered to the animal in an amount effective to treat or prevent fibrosis in the animal. The animal may be a mammal, and the mammal may be a primate, including human and non-human primates. In general, the mesenchymal stem cells are administered in an amount of from about $1 \times 10^5$ cells/kg to about $1 \times 10^7$ cells/kg. In another embodiment, the mesenchymal stem cells are administered in an amount of from about $1 \times 10^6$ cells/kg to about $5 \times 10^6$ cells/kg. The exact amount of mesenchymal stem cells to be administered is dependent upon a variety of factors, including the age, weight, and sex of the patient, and the extent and severity of the fibrosis being treated or prevented.

The mesenchymal stem cells may be administered in conjunction with an acceptable pharmaceutical carrier, as hereinabove described. The mesenchymal stem cells may be administered systemically, also as hereinabove described.

It is another object of the present invention to promote angiogenesis in a tissue or organ of an animal, wherein such tissue or organ is in need of angiogenesis.

Thus, in accordance with a further aspect of the present invention, there is provided a method of promoting angiogenesis in an organ or tissue of an animal. The method comprises administering to the animal mesenchymal stem cells in an amount effective to promote angiogenesis in an organ or tissue of the animal.

Angiogenesis is the formation of new blood vessels from a pre-existing microvascular bed.

The induction of angiogenesis may be used to treat coronary and peripheral artery insufficiency, and thus may be a noninvasive and curative approach to the treatment of coronary artery disease, ischemic heart disease, and peripheral artery disease. Angiogenesis may play a role in the treatment of diseases and disorders in tissue and organs other than the heart, as well as in the development and/or maintenance of organs other than the heart. Angiogenesis may provide a role in the treatment of internal and external wounds, as well as dermal ulcers. Angiogenesis also plays a role in embryo implantation, and placental growth, as well as the development of the embryonic vasculature. Angiogenesis also is essential for the coupling of cartilage resorption with bone formation, and is essential for correct growth plate morphogenesis.

Furthermore, angiogenesis is necessary for the successful engineering and maintenance of highly metabolic organs, such as the liver, where a dense vascular network is necessary to provide sufficient nutrient and gas transport.

The mesenchymal stem cells can be administered to the tissue or organ in need of angiogenesis by a variety of procedures. The mesenchymal stem cells may be administered systemically, such as by intravenous, intraarterial, or intraperitoneal administration, or the mesenchymal stem cells may be administered directly to the tissue or organ in need of angiogenesis, such as by direct injection into the tissue or organ in need of angiogenesis.

The mesenchymal stem cells may be from a spectrum of sources including autologous, allogeneic, or xenogeneic.

Although the scope of the present invention is not to be limited to any theoretical reasoning, it is believed that the mesenchymal stem cells, when administered to an animal, stimulate peripheral blood mononuclear cells (PBMCs) to produce vascular endothelial growth factor, or VEGF, which stimulates the formation of new blood vessels.

In one embodiment, the animal is a mammal. The mammal may be a primate, including human and non-human primates.

The mesenchymal stem cells, in accordance with the present invention, may be employed in the treatment, alleviation, or prevention of any disease or disorder which can be alleviated, treated, or prevented through angiogenesis. Thus, for example, the mesenchymal stem cells may be administered to an animal to treat blocked arteries, including those in the extremities, i.e., arms, legs, hands, and feet, as well as the neck or in various organs. For example, the mesenchymal stem cells may be used to treat blocked arteries which supply the brain, thereby treating or preventing stroke. Also, the mesenchymal stem cells may be used to treat blood vessels in embryonic and postnatal corneas and may be used to provide glomerular structuring. In another embodiment, the mesenchymal stem cells may be employed in the treatment of wounds, both internal and external, as well as the treatment of dermal ulcers found in the feet, hands, legs or arms, including, but not limited to, dermal ulcers caused by diseases such as diabetes and sickle cell anemia.

Furthermore, because angiogenesis is involved in embryo implantation and placenta formation, the mesenchymal stem sells may be employed to promote embryo implantation and prevent miscarriage.

In addition, the mesenchymal stem cells may be administered to an unborn animal, including humans, to promote the development of the vasculature in the unborn animal.

In another embodiment, the mesenchymal stem cells may be administered to an animal, born or unborn, in order to promote cartilage resorption and bone formation, as well as promote correct growth plate morphogenesis.

The mesenchymal stem cells are administered in an amount effective in promoting angiogenesis in an animal. The mesenchymal stem cells may be administered in an amount of from about $1 \times 10^5$ cells/kg to about $1 \times 10^7$ cells/kg. In another embodiment, the mesenchymal stem cells are administered in an amount of from about $1 \times 10^6$ cells/kg to about $5 \times 10^6$ cells/kg. The amount of mesenchymal stem cells to be administered is dependent upon a variety of factors, including the age, weight, and sex of the patient, the disease or disorder to be treated, alleviated, or prevented, and the extent and severity thereof.

The mesenchymal stem cells may be administered in conjunction with an acceptable pharmaceutical carrier. For example, the mesenchymal stem cells may be administered as a cell suspension in a pharmaceutically acceptable liquid medium for injection. Injection can be local, i.e., directly into the tissue or organ in need of angiogenesis, or systemic.

The mesenchymal stem cells may be genetically engineered with one or more polynucleotides encoding a therapeutic agent. The polynucleotides may be delivered to the mesenchymal stem cells via an appropriate expression vehicle. Expression vehicles which may be employed to genetically engineer the mesenchymal stem cells include, but are not limited to, retroviral vectors, adenoviral vectors, and adeno-associated virus vectors.

The selection of an appropriate polynucleotide encoding a therapeutic agent is dependent upon various factors, including the disease or disorder being treated, and the extent and severity thereof. Polynucleotides encoding therapeutic agents, and appropriate expression vehicles are described further in U.S. Pat. No. 6,355,239.

It is to be understood that the mesenchymal stem cells, when employed in the above-mentioned therapies and treatments, may be employed in combination with other therapeutic agents known to those skilled in the art, including, but not limited to, growth factors, cytokines, drugs such as anti-inflammatory drugs, and cells other than mesenchymal stem cells, such as dendritic cells, and may be administered with soluble carriers for cells such as hyalurionic acid, or in combination with solid matrices, such collagen, gelatin, or other biocompatible polymers, as appropriate.

It is to be understood that the methods described herein may be carried out in a number of ways and with various modifications and permutations thereof that are well known in the art. It also may be appreciated that any theories set forth as to modes of action or interactions between cell types should not be construed as limiting this invention in any manner, but are presented such that the methods of the invention can be understood more fully.

BRIEF DESCRIPTION OF SEVERAL VIEWS OF THE DRAWINGS

The invention now will be described with respect to the drawings, wherein.

EXAMPLES

Figure 1A:
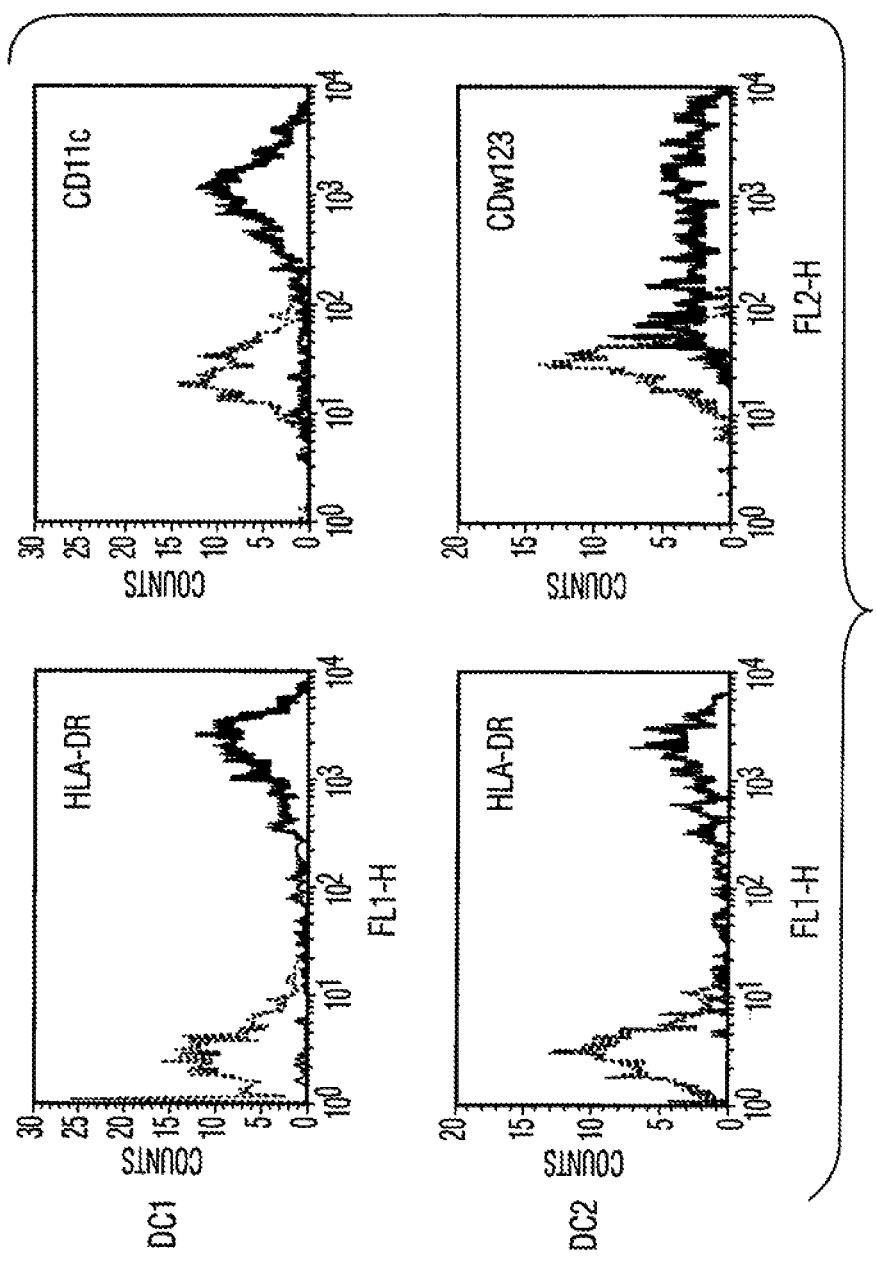
FIG. 1 MSCs modulate dendritic cell functions. (A) Flow cytometric analysis of mature monocytic DC1 cells using antibodies against HLA-DR and CD11c and of plasmacytoid DC2 cells using antibodies against HLA-DR and CD123 (IL-3 receptor). ( - - - ): isotype control; (–): FITC/PE conjugated antibodies. (B) MSCs inhibit TNF-α secretion (primary y-axis) and increase IL-10 secretion (secondary y-axis) from activated DC1 and DC2 respectively. (C) MSCs cultured with mature DC1 cells inhibit IFN-γ secretion (primary y-axis) by T cells and increase IL-4 levels (secondary y-axis) as compared to MSC or DC alone. The decreased production of pro-inflammatory IFN-γ and increased production of anti-inflammatory IL-4 in the presence of MSCs indicated a shift in the T cell population towards an anti-inflammatory phenotype.

The invention now will be described with respect to the following examples; it is to be understood, however, that the scope of the present invention is not to be limited thereby.

Example 1

Materials and Methods
Culture of Human MSCs

Human MSCs were cultured as described by Pittenger et al., Science, Vol. 284, pg. 143 (1999). Briefly, marrow samples were collected from the iliac crest of anonymous donors following informed consent by Poietics Technologies, Div of Cambrex Biosciences. MSCs were cultured in complete Dulbecco's Modified Eagle's Medium-Low Glucose (Life Technologies, Carlsbad, Calif.) containing 1% antibiotic-antimyotic solution (Invitrogen, Carlsbad, Calif.) and 10% fetal bovine serum (FBS, JRH BioSciences, Lenexa, Kans.). MSCs grew as an adherent monolayer and were detached with trypsin/EDTA (0.05% trypsin at 37° C. for 3 minutes). All MSCs used were previously characterized for multilineage potential and retained the capacity to differentiate into mesenchymal lineages (chondrocytic, adipogenic, and osteogenic) (Pittenger, et al., Science, Vol. 284, pg. 143 (1999)).

Isolation of Dendritic Cells

Peripheral blood mononuclear cells (PBMCs) were obtained from Poietics Technologies, Div of Cambrex Biosciences (Walkersville, Md.). Precursors of dendritic cells (DCs) of monocytic lineage (CD1c$^+$) were positively selected from PBMCs using a 2-step magnetic separation method according to Dzionek, et al., J. Immunol., Vol. 165, pg. 6037 (2000). Briefly, CD1c expressing B cells were magnetically depleted of CD19$^+$ cells using magnetic beads, followed by labeling the B-cell depleted fraction with biotin-labeled CD1c (BDCA1$^+$) and anti-biotin antibodies and separating them from the unlabeled cell fraction utilizing magnetic columns according to the manufacturer's instructions (Miltenyi Biotech, Auburn, Calif.). Precursors of DCs of plasmacytoid lineage were isolated from PBMCs by immuno-magnetic sorting of positively labeled antibody coated cells (BDCA2$^+$) (Miltenyi Biotech, Auburn, Calif.).

MSC.DC Culture

In most experiments, human MSCs and DCs were cultured in equal numbers for various time periods and cell culture supernatant collected and stored at −80° C. until further evaluation. In selected experiments, MSCs were cultured with mature DC1 or DC2 cells (1:1 MSC:DC ratio) for 3 days, and then the combined cultures (MSCs and DCs) were irradiated to prevent any proliferation. Next, antibody purified, naïve, allogeneic T cells (CD4$^+$, CD45RA$^+$) were added to the irradiated MSCs/DCs and cultured for an additional 6 days. The non-adherent cell fraction (purified T cells) was then collected from the cultures, washed twice and re-stimulated with PHA for another 24 hours, following which cell culture supernatants were harvested and analyzed for secreted IFN-γ and IL-4 by ELISA.

Isolation of NK Cells

Purified populations of NK cells were obtained by depleting non-NK cells that are magnetically labeled with a cocktail of biotin-conjugated monoclonal antibodies (anti-CD3, -CD14, -CD19, -CD36 and anti-IgE antibodies) as a primary reagent and anti-biotin monoclonal antibodies conjugated to Microbeads as secondary labeling reagent. The magnetically labeled non-NK cells were retained in MACS (Miltenyi Biotech, Auburn, Calif.) columns in a magnetic field, while NK cells passed through and were collected.

Isolation of $T_{Reg}$ Cell Population

The $T_{Reg}$ cell population was isolated using a 2-step isolation procedure. First non-CD4$^+$ T cells were indirectly magnetically labeled with a cocktail of biotin labeled antibodies and anti-biotin microbeads. The labeled cells were then depleted by separation over a MACS column (Miltenyi Biotech, Auburn, Calif.). Next, CD4$^+$ CD25$^+$ cells were directly labeled with CD25 microbeads and isolated by positive selection from the pre-enriched CD4$^+$ T cell fraction. The magnetically labeled CD4$^+$CD25$^+$ T cells were retained on the column and eluted after removal of the column from the magnetic field.

In order to determine whether the increased CD4+CD25+ population generated in the presence of MSCs were suppressive in nature, CD4+CD25+ $T_{reg}$ cell populations were isolated from PBMC or MSC+PBMC (MSC to PBMC ratio 1:10) cultures (cultured without any further stimulation for 3 days) using a 2-step magnetic isolation procedure. These cells were irradiated to block any further proliferation and used as stimulators in a mixed lymphocyte reaction (MLR), where responders were allogeneic PBMCs (stimulator to responder ratio 1:100) in the presence of PHA (2.5 µg/ml). The culture was carried out for 48 hours, following which $^3$H thymidine was added. Incorporated radioactivity was counted after 24 hours.

PBMCs were cultured in the absence or presence of MSCs (MSC to PBMC ratio 1:10), following which the non-adherent fraction was harvested and immunostained with FITC-labeled glucocorticoid-induced TNF receptor, or GITR, and PE-labeled CD4.

Generation of $T_H1/T_H2$ Cells

Peripheral blood mononuclear cells (PBMCs) were plated at 2×10$^6$ cells/ml for 45 min. at 37° C. in order to remove monocytes. Non-adherent fraction was incubated in the presence of plate-bound anti-CD3 (5 µg/ml) and anti-CD28 (1 µg/ml) antibodies under $T_H1$ (IL-2 (4 ng/ml)+IL-12 (5 ng/ml)+anti-IL-4 (1 µg/ml)) or $T_H2$ (IL-2 (4 ng/ml)+IL-4 (4 ng/ml)+anti-IFN-γ (1 µg/ml)) conditions for 3 days in the presence or absence of MSCs. The cells were washed and then re-stimulated with PHA (2.5 µg/ml) for another 24 or 48 hours, following which levels of IFN-γ and IL-4 were measured in culture supernatants by ELISA (R&D Systems, Minneapolis, Minn.).

Analysis of Levels of VEGF, PGE$_2$ and Pro-MMP-1 in Culture Supernatant of MSCs.

Using previously characterized human MSCs, the levels of Interleukin-6 (IL-6), VEGF, lipid mediator prostaglandin E$_2$ (PGE$_2$), and matrix metalloproteinase 1 (pro-MMP-1) were analyzed in culture supernatant of MSCs cultured for 24 hours in the presence or absence of PBMCs (MSC to PBMC ratio 1:10).

Proliferation of PBMCs

Purified PBMCs were prepared by centrifuging leukopack (Cambrex, Walkersville, Md.) on Ficoll-Hypaque (Lymphoprep, Oslo, Norway). Separated cells were cultured (in triplicates) in the presence or absence of MSCs (plated 3-4 hours prior to PBMC addition to allow them to settle) for 48 hours in presence of the mitogen PHA (Sigma Chemicals, St. Louis, Mo.). In selected experiments, PBMCs were resuspended in medium containing $PGE_2$ inhibitors Indomethacin (Sigma Chemicals, St. Louis, Mo.) or NS-938 (Cayman Chemicals, Ann Arbor, Mich.). ($^3$H)-thymidine was added (20 µl in a 200 µl culture) and the cells harvested after an additional 24 hour culture using an automatic harvester. The effects of MSCs or $PGE_2$ blockers were calculated as the percentage of the control response (100%) in presence of PHA.

Quantitative RT-PCR

Total RNA from cell pellets were prepared using a commercially available kit (Qiagen, Valencia, Calif.) and according to the manufacturer's instructions. Contaminating genomic DNA was removed using the DNA-free kit (Ambion, Austin, Tex.). Quantitative RT-PCR was performed on a MJ Research Opticon detection system (South San Francisco, Calif.) using QuantiTect SYBR Green RT-PCR kit (Qiagen, Valencia, Calif.) with primers at concentration of 0.5 µM. Relative changes in expression levels in cells cultured under different conditions were calculated by the difference in Ct values (crossing point) using β-actin as internal control. The sequence for COX-1 and COX-2 specific primers were: COX-1: 5'-CCG GAT GCC AGT CAG GAT GAT G-3'(forward) (SEQ ID NO:1), 5'-CTA GAC AGC CAG ATG CTG ACA G-3' (reverse) (SEQ ID NO:2); COX-2: 5'-ATC TAC CCT CCT CAA GTC CC-3' (forward) (SEQ ID NO:3), 5'-TAC CAG AAG GGC AGG ATA CAG-3' (reverse) (SEQ ID NO:4).

Increasing numbers of allogeneic PBMCs were incubated with constant numbers of MSCs (2,000 cells/well) plated on a 96-well plate in the presence of PHA (2.5 µg/ml) for 72 hours, and $^3$H thymidine incorporation (counts per minute, cpm) was determined. The PBMCs and MSCs were cultured at ratios of MSC:PBMC of 1:1, 1:3, 1:10, 1:30, and 1:81.

Results

In the present studies, the interaction of human MSCs with isolated immune cell populations, including dendritic cells (DC1 and DC2), effector T cells ($T_H1$ and $T_H2$) and NK cells was examined. The interaction of MSCs with each immune cell type had specific consequences, suggesting that MSCs may modulate several steps in the immune response process. The production of secreted factor(s) that modulate and may be responsible for MSC immuno-modulatory effects was evaluated and prostaglandin synthesis was implicated.

Figure 1B:
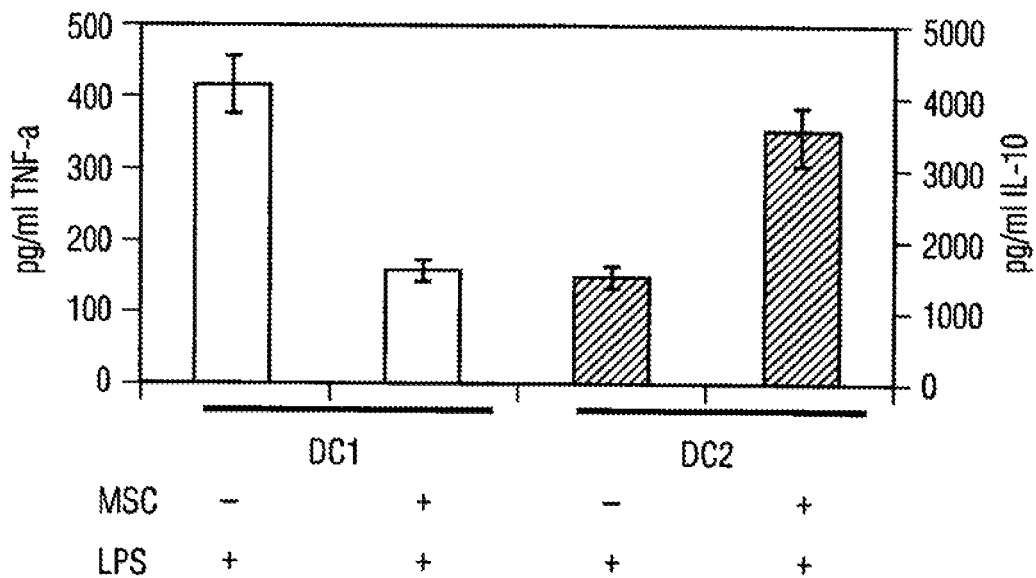
Figure 1C:
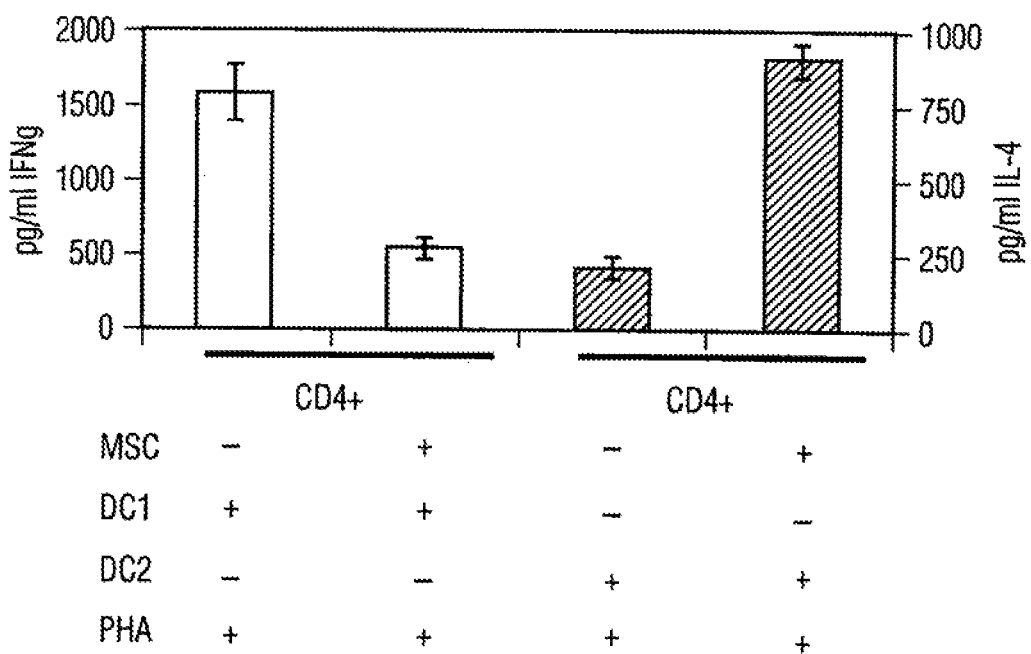

Myeloid (DC1) and plasmacytoid (DC2) precursor dendritic cells were isolated by immuno-magnetic sorting of BDCA1$^+$ and BDCA2$^+$ cells respectively and matured by incubation with GM-CSF and IL-4 (1×10$^3$ IU/ml and 1×10$^3$ IU/ml, respectively) for DC1 cells, or IL-3 (10 ng/ml) for DC2 cells. Using flow cytometry, DC1 cells were HLA-DR$^+$ and CD11c$^+$, whereas DC2 cells were HLA-DR$^+$ and CD123$^+$ (FIG. 1A). In the presence of the inflammatory agent bacterial lipopolysaccharide (LPS, 1 ng/ml), DC1 cells produced moderate levels of TNF-α but when MSCs were present (ratios examined 1:1 and 1:10), there was >50% reduction in TNF-α secretion (FIG. 1B). On the other hand, DC2 cells produced IL-10 in the presence of LPS and its levels were increased greater than 2-fold upon MSC:DC2 co-culture (1:1) (FIG. 1B). Therefore, the MSCs modified the cytokine profile of activated DCs in culture towards a more tolerogenic phenotype. Additionally, activated DCs, when cultured with MSCs, were able to reduce IFN-γ and increase IL-4 levels secreted by naïve CD$^{4+}$ T cells (FIG. 1C) suggesting a MSC-mediated shift from pro-inflammatory to anti-inflammatory T cell phenotype.

Figure 2A:
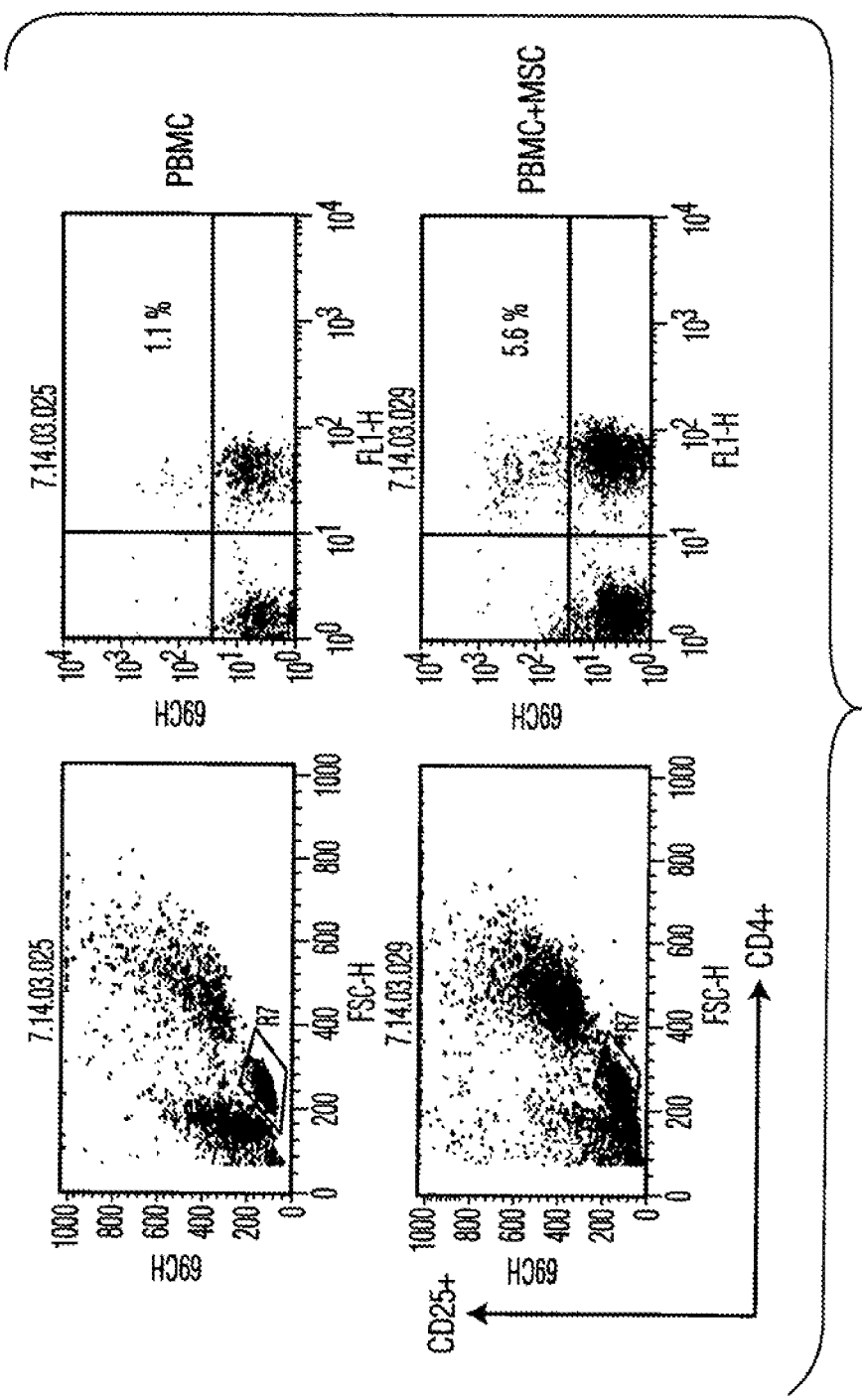
FIG. 2 MSCs inhibit pro-inflammatory effector T cell function. (A) Flow cytometric analysis of $T_{Reg}$ cell numbers (in %) by staining PBMCs or non-adherent fraction in MSC+PBMC culture (MSC+PBMC) with FITC-conjugated CD4 (x-axis) and PE conjugated CD25 (y-axis) antibodies. Gates were set based on isotype control antibodies as background. Graphs are representative of 5 independent experiments. (B) $T_H1$ cells generated in presence of MSCs secreted reduced levels of IFN-γ (primary y-axis) and $T_H2$ cells generated in presence of MSCs secreted increased amounts of IL-4 (secondary y-axis) in cell culture supernatants. (C) MSCs inhibit IFN-γ secretion from purified NK cells cultured for 0, 24, or 48 hours in a 24-well plate. Data shown are mean±SD cytokine secretion in one experiment and are representative of 3 independent experiments.
Figure 2B:
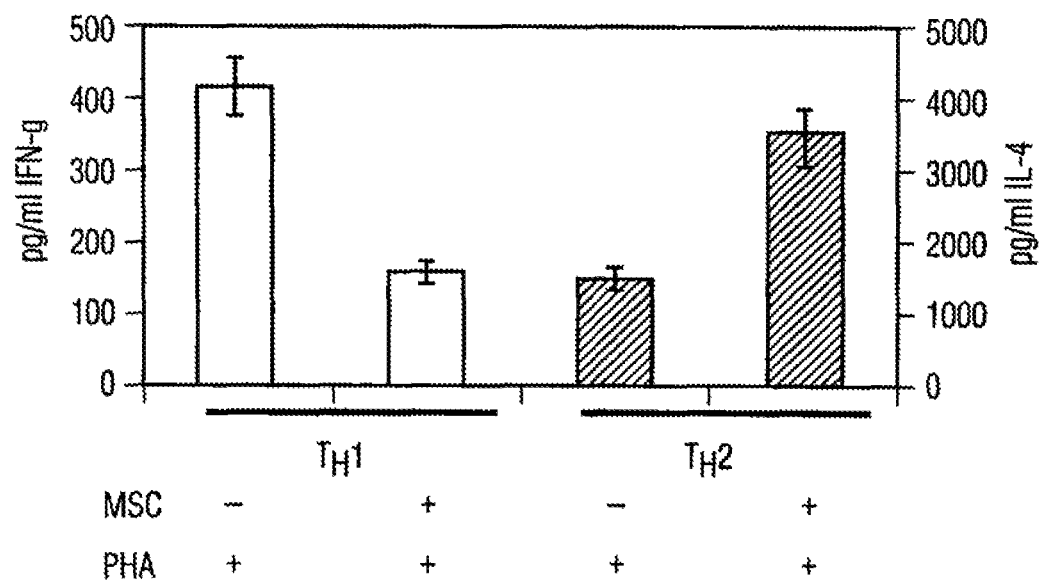
Figure 3A:
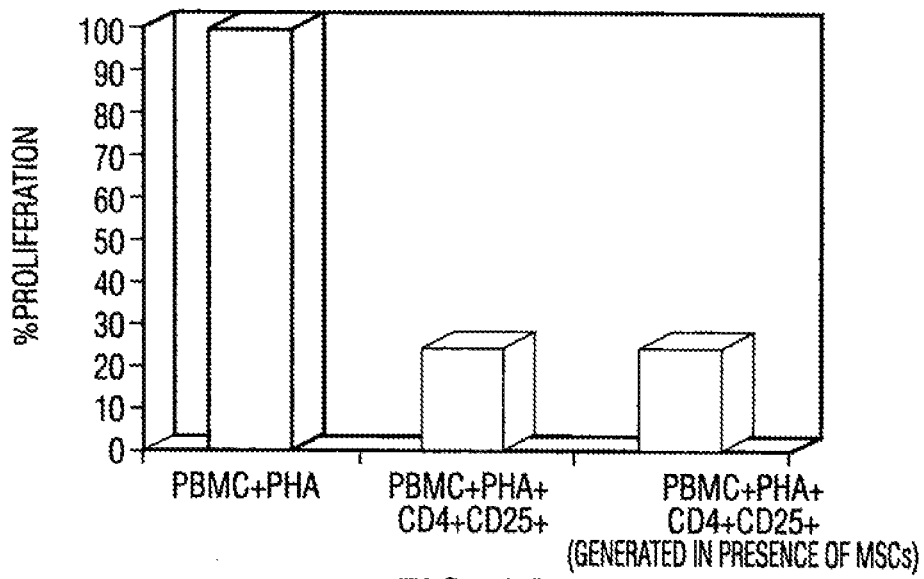
FIG. 3 MSCs lead to increased numbers of $T_{reg}$ cell population and increased GITR expression. (A) A $CD4^+$ $CD25^+$ $T_{reg}$ cell population from PBMC or MSC+PBMC (MSC to PBMC ratio 1:10) cultures (cultured without any further stimulation for 3 days) was isolated using a 2-step magnetic isolation procedure. These cells were irradiated (to block any further proliferation) and used as stimulators in a mixed lymphocyte reaction (MLR), where responders were allogeneic PBMCs (stimulator to responder ratio 1:100) in the presence of phytohemagglutinin (PHA) (2.5 mg/ml). The cells were cultured for 48 hours, following which $^3H$ thymidime was added, and incorporated radioactivity was counted after 24 hours. The results showed that the $T_{reg}$ population generated in the presence of MSCs (lane 3) was similar functionally to the $T_{reg}$ cells generated in the absence of MSCs (lane 2). (B) PBMCs were cultured for 3 days in the absence (top plot) or presence (bottom plot) of MSCs (MSC to PBMC ratio 1:10), following which the non-adherent fraction was harvested and immunostained with FITC-labeled GITR and PE-labeled CD4. Results show a greater than twofold increase in GITR expression in cells cultured in the presence of MSCs.
Figure 3B:
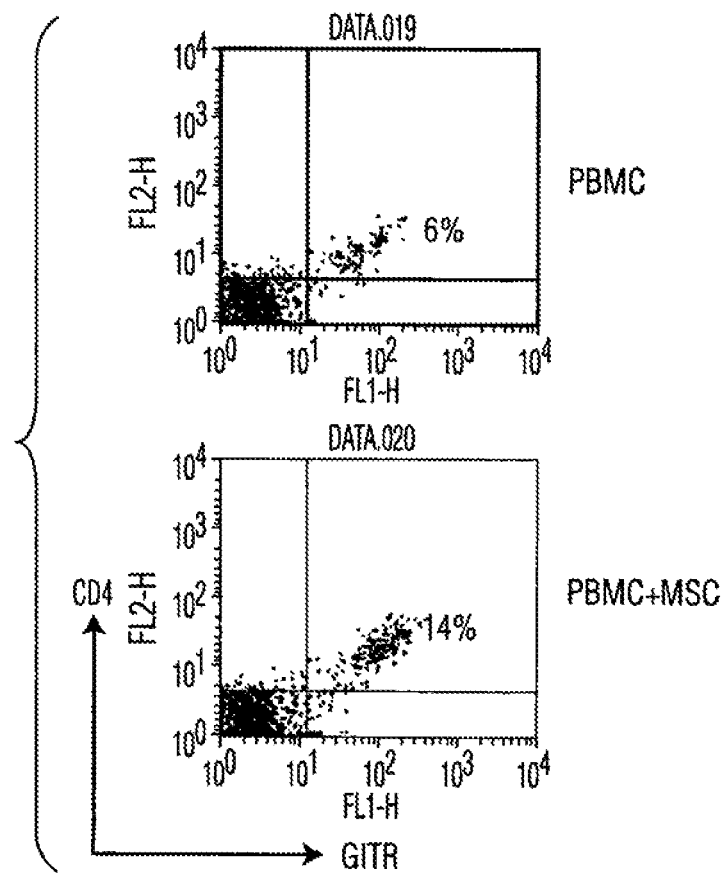

As increased IL-10 secretion plays a role in generation of regulatory cells (Kingsley, et al., *J. Immunol.*, Vol. 168, pg. 1080 (2002)), T-regulatory cells ($T_{Reg}$) were quantified by flow cytometry in co-cultures of PBMCs and MSCs. Upon culture of PBMCs with MSCs for 3-5 days, there was an increase in $T_{Reg}$ cell numbers as determined by staining of PBMCs with anti-CD4 and anti-CD25 antibodies (FIG. 2A), further supporting a MSC-induced tolerogenic response. The CD4$^+$CD25$^+$ $T_{Reg}$ cell population, generated in presence of MSCs expressed increased levels of gluocorticoid-induced TNF receptor (GITR), a cell surface receptor expressed on $T_{Reg}$ cell populations, and was suppressive in nature as it suppressed allogeneic T cell proliferation (FIG. 3A,B). Next, MSCs were investigated as to their direct ability to affect T cell differentiation. Using antibody selected purified T cells (CD4$^+$ Th cells), IFN-γ producing $T_H1$ and IL-4 producing $T_H2$ cells were generated in presence or absence of MSCs. When MSCs were present during differentiation, there was reduced IFN-γ secretion by $T_H1$ cells and increased IL-4 secretion by $T_H2$ cells (FIG. 2B). No significant change in IFN-γ or IL-4 levels were seen when MSCs were added to the culture after Th cells had differentiated (at 3 days) into effector $T_H1$ or $T_H2$ types (data not shown). These experiments suggest that MSCs can affect effector T cell differentiation directly and alter the T cell cytokine secretion towards a humoral phenotype.

Figure 2C:
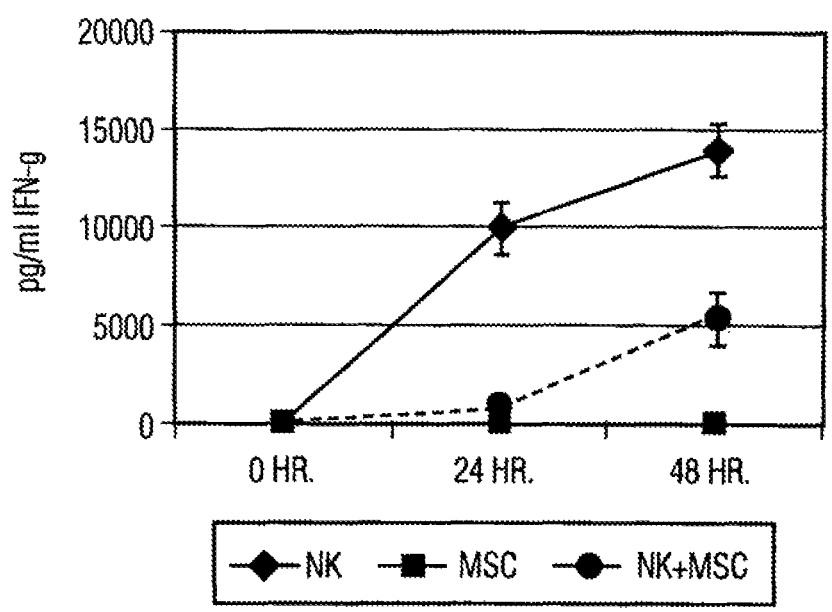

Similarly, when MSCs were cultured with purified NK cells (CD3−, CD14−, CD19−, CD36$^−$) at a ratio 1:1 for different time periods (0-48 hrs), there was decreased IFN-γ secretion in the culture supernatant (FIG. 2C), thereby suggesting that MSCs can modulate NK cell functions also.

Figure 4A:
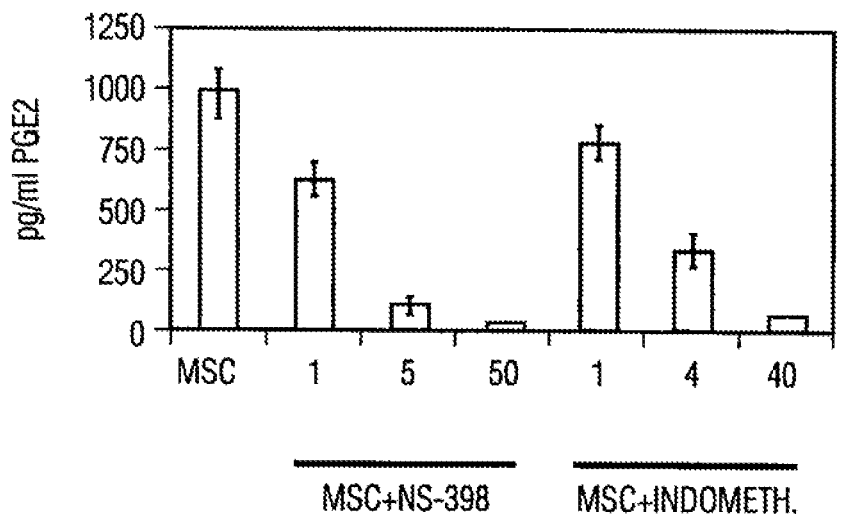
FIG. 4 MSCs produce $PGE_2$ and blocking $PGE_2$ reverses MSC-mediated immuno-modulatory effects. (A) $PGE_2$ secretion (mean±SD) in culture supernatants obtained from MSCs cultured in the presence or absence of $PGE_2$ blockers NS-398 or indomethacin (Indometh.) at various concentrations. Inhibitor concentrations are in µM and data presented are values obtained after 24 hour culture (B) COX-1 and COX-2 expression in MSCs and PBMCs using real-time RT-PCR. MSCs expressed significantly higher levels of COX-2 as compared to PBMCs, and when MSCs were cultured in presence of PBMCs, there was a >3-fold increase in COX-2 expression in MSCs. Representative data from 1 of 3 independent experiments is shown. The MSC+PBMC cultures were setup in a trans-well chamber plate where MSCs were plated onto the bottom chamber and PBMCs onto the top chamber. (C) Presence of $PGE_2$ blockers indomethacin (Ind.) or NS-398 increases TNF-α secretion from activated DCs (□) and IFN-γ secretion from $T_H1$ cells (■) as compared to controls. Data were calculated as % change from cultures generated in absence of MSCs and $PGE_2$ inhibitors (C) Presence of $PGE_2$ blockers indomethacin (Indo) and NS-398 during MSC-PBMC co-culture (1:10) reverses MSC-mediated anti-proliferative effects on PHA-treated PBMCs. Data shown are from one experiment and are representative of 3 independent experiments.
Figure 4B:
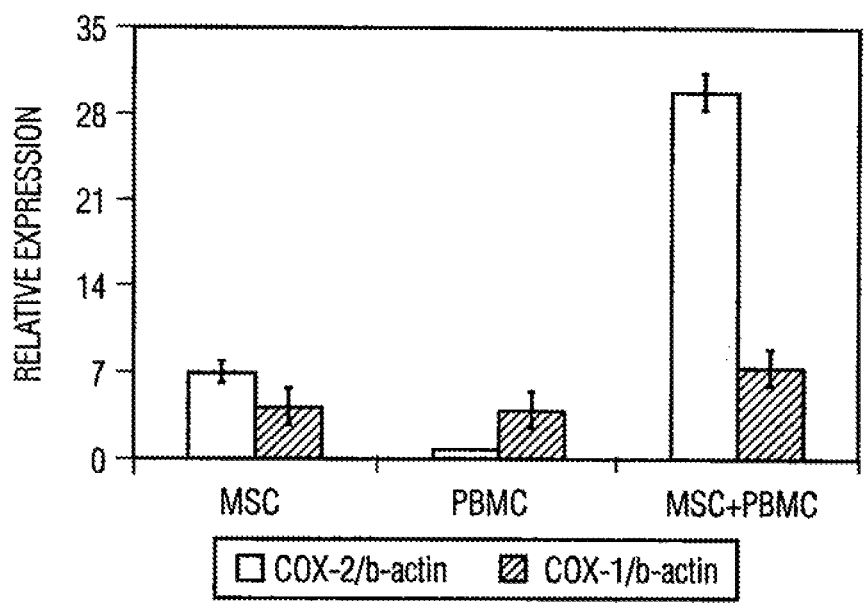
Figure 4C:
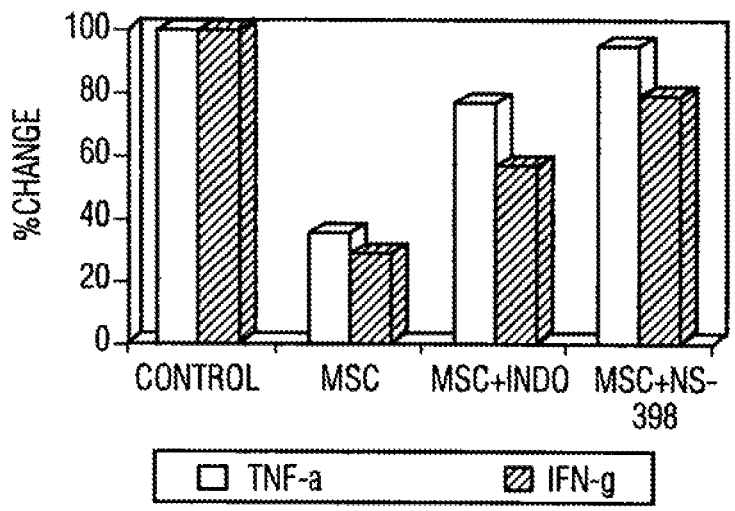
Figure 4D:
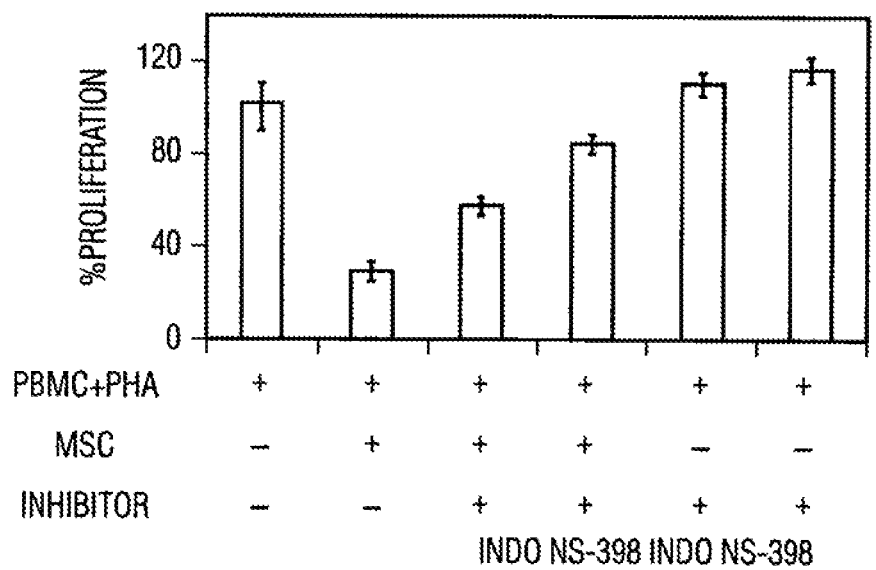
Figure 5:
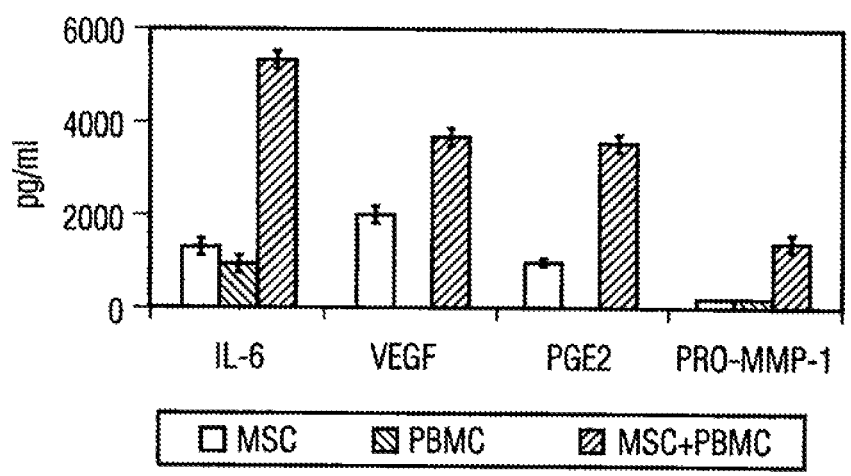
FIG. 5 Constitutive MSC cytokine secretion is elevated in the presence of allogeneic PBMCs. Using previously characterized human MSCs, the levels of the cytokines IL-6 and VEGF, lipid mediator $PGE_2$, and matrix metalloproteinase 1 (pro-MMP-1) in culture supernatant of MSCs cultured for 24 hours in the presence (hatched bars) or absence (open bars) of PBMCs (MSC to PBMC ratio 1:10) were analyzed. The MSCs produced IL-6, VEGF, and $PGE_2$ constituitively, and the levels of these factors increased upon co-culture with PBMCs, thereby suggesting that MSCs may play a role in modulating immune functions in an inflammatory setting.
Figure 6:
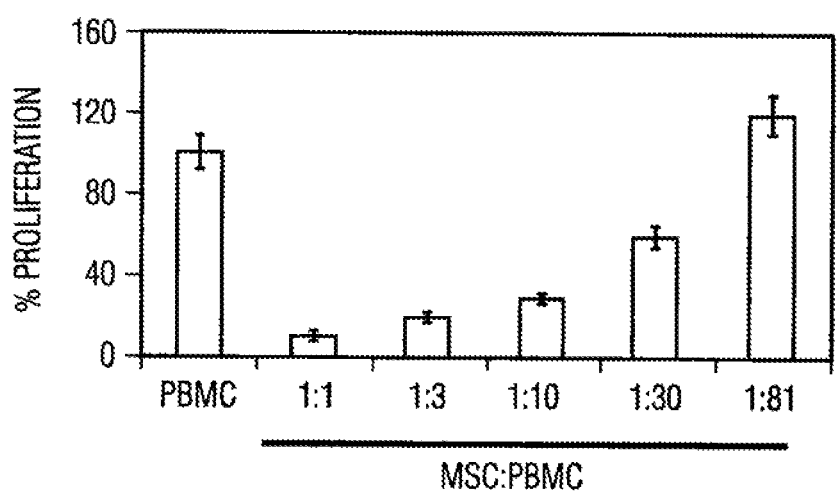
FIG. 6 MSCs inhibit mitogen-induced T-cell proliferation in a dose-dependent manner. Increasing numbers of allogeneic PBMCs were incubated with constant numbers of MSCs (2,000 cells/well) plated on a 96-well plate in the presence or absence of PHA (2.5 mg/ml) for 72 hours, and $^3H$ thymidine incorporation determined (in counts per minute, or cpm). There was a dose-dependent inhibition of the proliferation of PHA-treated PBMCs in the presence of MSCs. Representative results from 1 of 3 independent experiments are shown. Similar results were reported by LeBlanc, et al., *Scand J. Immunol.*, Vol. 57, pg. 11 (2003).

Previous work has indicated that MSCs modify T-cell functions by soluble factor(s) (LeBlanc, et al., *Exp. Hematol.*, Vol. 31, pg. 890 (2003); Tse, et al., *Transplantation*, Vol. 75, pg. 389 (2003)). It was observed that the MSCs secreted several factors, including IL-6, prostaglandin $E_2$, VEGF and proMMP-1 constitutively, and the levels of each increased upon culture with PBMCs (FIG. 5). In order to investigate MSC-derived factors leading to inhibition of TNF-α and increase of IL-10 production by DCs, the potential role of prostaglandin $E_2$ was investigated, as it has been shown to inhibit TNF-α production by activated DCs (Vassiliou, et al., *Cell. Immunol.*, Vol. 223, pg. 120 (2003)). Conditioned media from MSC culture (24 hour culture of 0.5×10$^6$ cells/ml) contained approx. 1000 µg/ml of $PGE_2$ (FIG. 4A). There was no detectable presence of known inducers of $PGE_2$ secretion, e.g., TNF-α, IFN-γ or IL-1β (data not shown) in the culture supernatant indicating a constitutive secretion of $PGE_2$ by MSCs. The $PGE_2$ secretion by hMSCs was inhibited 60-90% in the presence of known inhibitors of $PGE_2$ production, NS-398 (5 µM) and indomethacin (4 µM) (FIG. 4A). As the release of $PGE_2$ secretion occurs as a result of enzymatic activity of constitutively active cycloxygenase enzyme 1 (COX-1) and inducible cycloxygenase enzyme 2 (COX-2) (Harris, et al., *Trends Immunol.*, Vol. 23, pg. 144 (2002)) the mRNA expression for COX-1 and COX-2 in MSCs and PBMCs using trans-well culture system was analyzed. MSCs expressed significantly higher levels of COX-2 as compared to PBMCs and the expression levels increase >3-fold upon co-culture of MSCs and PBMCs (MSC to PBMC ratio 1:10) for 24 hours (FIG. 4B). Modest changes in COX-1 levels were seen suggesting that the increase in $PGE_2$ secretion upon MSC-PBMC co-culture (FIG. 5) is mediated by COX-2 up-regulation. To investigate whether the immunomodulatory effects of MSC on DCs and T-cells were mediated by $PGE_2$, MSCs were cultured with activated dendritic cells (DC1) or $T_H1$ cells in the presence of $PGE_2$ inhibitors NS-398 or indomethacin. The presence of NS-398 or indomethacin increased TNF-α secretion by DC1s, and IFN-γ secretion from $T_H1$ cells (FIG. 4C), respectively, suggesting that MSC effects on immune cell types may be mediated by secreted $PGE_2$. Recent studies have shown that MSCs inhibit T-cell proliferation induced by various stimuli (DeNicola, et al., *Blood*, Vol. 99, pg. 3838 (2002); LeBlanc, et al., *Scand. J. Immunol.*, Vol. 57, pg. 11 (2003)). It was observed that MSCs inhibit mitogen-induced T cell proliferation in a dose-dependent manner (FIG. 6) and when $PGE_2$ inhibitors NS-398 (5 μM) or indomethacin (4 μM) were present, there was a >70% increase in ($^3$H) thymidine incorporation by PHA-treated PBMCs in MSC containing cultures as compared to controls without inhibitors (FIG. 4D).

Figure 7:
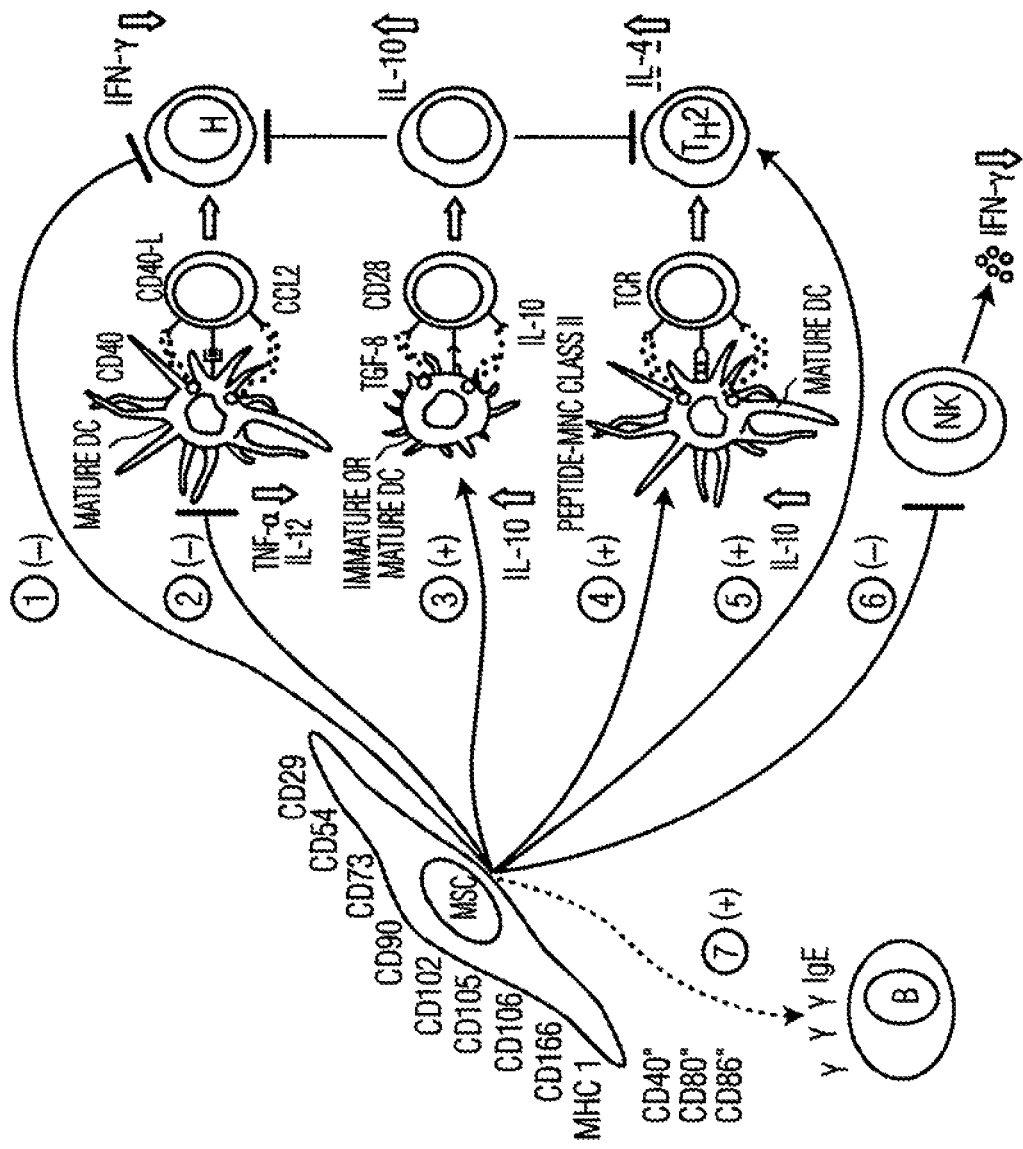
FIG. 7 Schematic diagram of proposed MSC mechanism of action. MSCs mediate their immuno-modulatory effects by affecting cells from both the innate (DCs-pathways 2-4; and NK-pathway 6) and adaptive (T-pathways 1 and 5 and B-pathway 7) immune systems. In response to an invading pathogen, immature DCs migrate to the site of potential entry, mature and acquire an ability to prime naïve T cells (by means of antigen specific and co-stimulatory signals) to become protective effector T cells (cell-mediated $T_H1$ or humoral $T_H2$ immunity). During MSC-DC interaction, MSCs, by means of direct cell-cell contact or via secreted factor, may alter the outcome of immune response by limiting the ability of DCs to mount a cell-mediated response (pathway 2) or by promoting the ability to mount a humoral response (pathway 4). Also, when mature effector T cells are present, MSCs may interact with them to skew the balance of $T_H1$ (pathway 1) responses towards $T_H2$ responses (pathway 5), and probably towards an increased IgE producing B cell activity (pathway 7), desirable outcomes for suppression of GvHD and autoimmune disease symptoms. MSCs in their ability to result in an increased generation of $T_{Reg}$ population (pathway 3) may result in a tolerant phenotype and may aid a recipient host by dampening bystander inflammation in their local micro-environment. Dashed line ( - - - ) represents proposed mechanism.

In summary, a model of MSC interaction with other immune cell types (FIG. 7) is proposed. When mature T cells are present, MSCs may interact with them directly and inhibit the pro-inflammatory IFN-γ production (pathway 1) and promote regulatory T cell phenotype (pathway 3) and anti-inflammatory $T_H2$ cells (pathway 5). Further, MSCs can alter the outcome of the T cell immune response through DCs by secreting $PGE_2$, inhibiting pro-inflammatory DC1 cells (pathway 2) and promoting anti-inflammatory DC2 cells (pathway 4) or regulatory DCs (pathway 3). A shift towards $T_H2$ immunity in turn, suggests a change in B cell activity towards increased generation of IgE/IgG1 subtype antibodies (pathway 7). MSCs, by their ability to inhibit IFN-γ secretion from NK cells likely modify NK cell function (pathway 6). This model of MSC: Immune cell interactions is consistent with the experimentation performed in several other laboratories (LeBlanc, et al., *Exp. Hematol.*, Vol. 31, pg. 890 (2003); Tse, et al., *Transplantation*, Vol. 75, pg. 389 (2003); DiNicola, et al., *Blood*, Vol. 99, pg. 3838 (2002)). Further examination of the proposed mechanisms is underway and animal studies are now necessary to examine the in vivo effects of MSC administration.

Example 2

Mesenchymal stem cells were given to a 33-year-old female patient suffering from severe Grade IV gastrointestinal graft-versus-host disease (GVHD). The patient was refractory to all other GVHD treatments. Endoscopic views of the patient's colon showed areas of ulceration and inflammation prior to treatment. Histology of the patient's colon showed that the graft-versus-host disease had destroyed the vast majority of the patient's intestinal crypts, prior to treatment.

The patient was given an intravenous infusion of allogeneic mesenchymal stem cells in 50 ml of Plasma Lyte A in an amount of $3 \times 10^6$ cells per kilogram of body weight.

The patient was evaluated at two weeks post-infusion. At two weeks post-infusion, an endoscopic view of the patient's colon showed that the areas of inflammation and ulceration visible prior to treatment were resolved. In addition, a biopsy of the patient's colon showed significant regeneration of intestinal crypts. Thus, the administration of the mesenchymal stem cells to the patient resulted in a significant reduction in the inflammatory component of gastrointestinal graft-versus-host disease, and resulted in the regeneration of new functional intestinal tissue.

The disclosures of all patents, publications, including published patent applications, depository accession numbers, and database accession numbers are hereby incorporated by reference to the same extent as if each patent, publication, depository accession number, and database accession number were specifically and individually incorporated by reference.

It is to be understood, however, that the scope of the present invention is not to be limited to the specific embodiments described above. The invention may be practiced other than as particularly described and still be within the scope of the accompanying claims.

The invention claimed is:

1. A method of reducing inflammation associated with graft-versus-host disease in a human in need thereof, comprising the step of
   intravenously or intraarterially administering to a human having graft-versus-host disease associated inflammation a suspension of cells in a therapeutic amount effective to reduce the inflammation, and
   wherein the cells comprise genetically unmanipulated cultured allogeneic mesenchymal stem cells.

2. The method of claim 1, wherein the suspension further comprises an acceptable pharmaceutical carrier.

3. The method of claim 2, wherein the acceptable pharmaceutical carrier is a pharmaceutically acceptable liquid medium for injection.

4. The method of claim 1, wherein the suspension is administered in an amount of from about $1\times10^5$ cells/kg to about $1\times10^7$ cells/kg.

5. The method of claim 1, wherein the suspension is administered in an amount of from about $1\times10^6$ cells/kg to about $5\times10^6$ cells/kg.

6. The method of claim 1, wherein the inflammation is inflammation in the gut.

7. The method of claim 1, wherein the cells are isolated from marrow.

8. The method of claim 7, wherein the marrow is iliac crest marrow.

9. The method of claim 1, wherein the administration is intravenous.

10. The method of claim 1, wherein the administration is intraarterial.

11. A method of reducing inflammation in the gut of a human comprising intravenously or intraarterially administering to a human suffering from inflammation of the gut a suspension of cells in a therapeutically effective amount to reduce the inflammation, wherein the cells comprise genetically unmanipulated cultured allogeneic mesenchymal stem cells.

12. The method of claim 11, wherein the suspension further comprises an acceptable pharmaceutical carrier.

13. The method of claim 12, wherein the acceptable pharmaceutical carrier is a pharmaceutically acceptable liquid medium for injection.

14. The method of claim 11, wherein the suspension is administered in an amount of from about $1\times10^5$ cells/kg to about $1\times10^7$ cells/kg.

15. The method of claim 11, wherein the suspension is administered in an amount of from about $1\times10^6$ cells/kg to about $5\times10^6$ cells/kg.

16. The method of claim 11, wherein the cells are isolated from marrow.

17. The method of claim 16, wherein the marrow is iliac crest marrow.

18. The method of claim 11, wherein the administration is intravenous.

19. The method of claim 11, wherein the administration is intraarterial.

20. The method of claim 1, wherein the cells consist of genetically unmanipulated cultured allogeneic mesenchymal stem cells.

21. The method of claim 11, wherein the cells consist of genetically unmanipulated cultured allogeneic mesenchymal stem cells.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial
<220> FEATURE:
<223> OTHER INFORMATION: synthetic sequences and are primers for PCR
      derived from human COX-1
<220> FEATURE:
<221> NAME/KEY: misc_feature
<222> LOCATION: (1)..(22)
<223> OTHER INFORMATION: COX-1 forward primer

<400> SEQUENCE: 1
ccggatgcca gtcaggatga tg                                              22

<210> SEQ ID NO 2
<211> LENGTH: 22
<212> TYPE: DNA
<213> ORGANISM: Artificial
<220> FEATURE:
<223> OTHER INFORMATION: synthetic sequences and are primers for PCR
      derived from human COX-1
<220> FEATURE:
<221> NAME/KEY: misc_feature
<222> LOCATION: (1)..(22)
```

```
<223> OTHER INFORMATION: COX-1 reverse primer

<400> SEQUENCE: 2
ctagacagcc agatgctgac ag                                              22

<210> SEQ ID NO 3
<211> LENGTH: 20
<212> TYPE: DNA
<213> ORGANISM: artificial
<220> FEATURE:
<223> OTHER INFORMATION: synthetic sequences and are primers for PCR
      derived from human COX-2
<220> FEATURE:
<221> NAME/KEY: misc_feature
<222> LOCATION: (1)..(20)
<223> OTHER INFORMATION: COX-2 forward primer

<400> SEQUENCE: 3
atctaccctc ctcaagtccc                                                 20

<210> SEQ ID NO 4
<211> LENGTH: 21
<212> TYPE: DNA
<213> ORGANISM: Artificial
<220> FEATURE:
<223> OTHER INFORMATION: primer for PCR derived from human COX-2
<220> FEATURE:
<221> NAME/KEY: misc_feature
<222> LOCATION: (1)..(21)
<223> OTHER INFORMATION: COX-2 reverse primer

<400> SEQUENCE: 4
taccagaagg gcaggataca g                                               21
```